(12) United States Patent
Risk, Jr. et al.

(10) Patent No.: US 7,927,318 B2
(45) Date of Patent: Apr. 19, 2011

(54) WASTE CONTAINER FOR NEGATIVE PRESSURE THERAPY

(76) Inventors: James Robert Risk, Jr., Fountaintown, IN (US); Robert Petrosenko, Batesville, IN (US); Alexander B. Bitel, Cincinnati, OH (US); Jeffrey S. Lockwood, Batesville, IN (US)

( * ) Notice: Subject to any disclaimer, the term of this patent is extended or adjusted under 35 U.S.C. 154(b) by 0 days.

(21) Appl. No.: 11/230,988

(22) Filed: Sep. 20, 2005

(65) Prior Publication Data

US 2006/0015087 A1    Jan. 19, 2006

Related U.S. Application Data

(63) Continuation of application No. 10/267,358, filed on Oct. 9, 2002, now abandoned.

(60) Provisional application No. 60/328,542, filed on Oct. 11, 2001.

(51) Int. Cl.
*A61F 13/00* (2006.01)
*A61M 1/00* (2006.01)

(52) U.S. Cl. ........ 604/305; 604/304; 604/319; 604/320; 604/322

(58) Field of Classification Search .......... 604/317–319, 604/324, 304, 305, 307, 326, 320, 322
See application file for complete search history.

(56) References Cited

U.S. PATENT DOCUMENTS

| | | | |
|---|---|---|---|
| 774,529 A | 11/1904 | Nieschang | |
| 1,000,001 A | 8/1911 | Holz | |
| 1,355,846 A | 10/1920 | Rannells | |
| 1,385,346 A | 7/1921 | Taylor | |
| 1,709,520 A | 4/1929 | Chandler | |
| 1,936,129 A | 11/1933 | Fisk | |
| 2,078,180 A | 4/1937 | Kronenberg | |
| 2,195,771 A | 4/1940 | Estler | |
| 2,221,758 A | 11/1940 | Elmquist | |
| 2,305,289 A | 12/1942 | Coburg | 128/132 |
| 2,338,339 A | 1/1944 | LaMere et al. | |
| 2,443,481 A | 6/1948 | Sene | |
| 2,547,758 A | 4/1951 | Keeling | 128/349 |
| 2,560,915 A | 7/1951 | Bamberger | 128/350 |
| 2,573,791 A | 11/1951 | Howells | |
| 2,577,945 A | 12/1951 | Atherton | |

(Continued)

FOREIGN PATENT DOCUMENTS

AU    550575 A1    8/1982

(Continued)

OTHER PUBLICATIONS

Oosterbroek, R.E. et al, "A Micromachined Pressure/Flow-sensor" (Abstract only), http://www.ingentaconnect.com/content/els/09244247/1999/00000077/00000003/art00188, Sensors and Actuators A: vol. 77, No. 3, Nov. 2, 1999.*

(Continued)

*Primary Examiner* — Melanie J Hand (57) ABSTRACT

A system for treating a patient with a wound comprises a bandage, a receptacle, and a vacuum source. The bandage comprises a cover to seal about the wound and to define a space above the wound in which a vacuum is to be formed. The bandage further comprises a port providing communication with the space. The receptacle is connected to the port to receive exudate from the wound and is provided to be placed below the wound. The vacuum source is spaced apart from the receptacle, is connected to the receptacle, and is effective to provide a vacuum in the receptacle and in the space.

16 Claims, 4 Drawing Sheets

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | 128/72.2 |
| 2,969,057 A | 1/1961 | Simmons | 128/2 |
| 3,026,874 A | 3/1962 | Stevens | |
| 3,066,672 A | 12/1962 | Crosby, Jr. et al. | 128/276 |
| 3,315,665 A | 4/1967 | MacLeod | |
| 3,367,332 A | 2/1968 | Groves | |
| 3,382,867 A | 5/1968 | Reaves | |
| 3,430,631 A | 3/1969 | Abramson | 128/350 |
| 3,492,991 A | 2/1970 | Dyer, Jr. | |
| 3,520,300 A | 7/1970 | Flower, Jr. | |
| 3,528,416 A | 9/1970 | Chamberlain | |
| 3,568,675 A | 3/1971 | Harvey | |
| 3,585,742 A | 6/1971 | Tyler | |
| 3,599,639 A | 8/1971 | Spotz | |
| 3,610,238 A | 10/1971 | Rich, Jr. | |
| 3,623,087 A | 11/1971 | Gallichotte | |
| 3,626,087 A | 12/1971 | Tomioka | 178/5.4 |
| 3,648,692 A | 3/1972 | Wheeler | |
| 3,682,180 A | 8/1972 | McFarlane | 128/350 |
| 3,683,894 A | 8/1972 | Villari | |
| 3,721,244 A | 3/1973 | Elmaleh | |
| 3,752,158 A | 8/1973 | Kariher | |
| 3,753,439 A | 8/1973 | Brugarolas et al. | 128/350 |
| 3,782,377 A | 1/1974 | Rychlik | |
| 3,812,972 A | 5/1974 | Rosenblum | |
| 3,814,095 A | 6/1974 | Lubens | |
| 3,817,145 A | 6/1974 | Cohen | 84/471 |
| 3,823,720 A | 7/1974 | Tribble | 128/350 |
| 3,826,254 A | 7/1974 | Mellor | 128/133 |
| 3,831,588 A | 8/1974 | Rindner | |
| 3,860,008 A | 1/1975 | Miner et al. | 128/350 |
| 3,874,387 A | 4/1975 | Barbieri | |
| 3,903,882 A | 9/1975 | Barbieri | |
| 3,924,624 A * | 12/1975 | Schachet | 604/321 |
| 3,935,863 A | 2/1976 | Kliger | |
| 3,954,105 A | 5/1976 | Nordby et al. | |
| 3,982,546 A | 9/1976 | Friend | |
| 4,004,590 A | 1/1977 | Muriot | |
| 4,013,076 A | 3/1977 | Puderbaugh et al. | |
| RE29,319 E | 7/1977 | Nordby et al. | |
| RE29,321 E * | 7/1977 | Holbrook | 215/309 |
| 4,058,123 A | 11/1977 | May | 128/278 |
| 4,080,970 A | 3/1978 | Miller | |
| 4,096,853 A | 6/1978 | Weigand | 128/2 |
| 4,112,947 A | 9/1978 | Nehring | |
| 4,139,004 A | 2/1979 | Gonzalez, Jr. | |
| 4,149,541 A | 4/1979 | Gammons et al. | |
| 4,165,748 A | 8/1979 | Johnson | 128/348 |
| 4,178,974 A | 12/1979 | Levin | |
| 4,184,510 A | 1/1980 | Murry et al. | 137/565 |
| 4,191,204 A | 3/1980 | Nehring | |
| 4,219,021 A | 8/1980 | Fink | 128/214 |
| 4,224,941 A | 9/1980 | Stivala | |
| 4,233,969 A | 11/1980 | Lock et al. | 128/156 |
| 4,245,630 A | 1/1981 | Lloyd et al. | 128/155 |
| 4,250,882 A | 2/1981 | Adair | |
| 4,256,109 A | 3/1981 | Nichols | 128/276 |
| 4,261,363 A | 4/1981 | Russo | 128/350 |
| 4,275,721 A | 6/1981 | Olson | |
| 4,284,079 A | 8/1981 | Adair | 128/295 |
| 4,297,995 A | 11/1981 | Golub | |
| 4,333,468 A | 6/1982 | Geist | 128/348 |
| 4,341,209 A | 7/1982 | Schaar | |
| 4,364,394 A | 12/1982 | Wilkinson | 604/96 |
| 4,373,519 A | 2/1983 | Errede et al. | |
| 4,382,441 A | 5/1983 | Svedman | |
| 4,392,853 A | 7/1983 | Muto | 604/171 |
| 4,392,858 A | 7/1983 | George et al. | 604/187 |
| 4,399,816 A | 8/1983 | Spangler | |
| 4,419,097 A | 12/1983 | Rowland | 604/174 |
| 4,445,897 A | 5/1984 | Ekbladh et al. | 604/280 |
| 4,457,755 A | 7/1984 | Wilson | |
| 4,460,370 A | 7/1984 | Allison et al. | |
| 4,465,062 A | 8/1984 | Versaggi et al. | |
| 4,465,485 A | 8/1984 | Kashmer et al. | 604/320 |
| 4,469,092 A | 9/1984 | Marshall et al. | |
| 4,475,909 A | 10/1984 | Eisenberg | 604/349 |
| 4,480,638 A | 11/1984 | Schmid | 128/155 |
| 4,508,533 A | 4/1985 | Abramson | 604/35 |
| 4,525,156 A | 6/1985 | Benusa et al. | 604/28 |
| 4,525,166 A | 6/1985 | Leclerc | |
| 4,525,374 A | 6/1985 | Vaillancourt | 427/2 |
| 4,533,352 A | 8/1985 | Van Beek et al. | |
| 4,533,419 A | 8/1985 | Pieslak et al. | |
| 4,540,412 A | 9/1985 | Van Overloop | |
| 4,543,100 A | 9/1985 | Brodsky | 604/180 |
| 4,548,202 A | 10/1985 | Duncan | 128/334 |
| 4,551,139 A | 11/1985 | Plaas et al. | 604/290 |
| 4,553,967 A | 11/1985 | Ferguson et al. | |
| 4,569,348 A | 2/1986 | Hasslinger | 604/179 |
| 4,569,674 A | 2/1986 | Phillips et al. | |
| 4,573,965 A | 3/1986 | Russo | |
| 4,579,555 A | 4/1986 | Russo | |
| 4,596,564 A | 6/1986 | Spetzler et al. | 604/281 |
| 4,605,399 A | 8/1986 | Weston et al. | |
| 4,608,041 A | 8/1986 | Nielsen | |
| 4,614,794 A | 9/1986 | Easton et al. | 530/356 |
| 4,624,656 A | 11/1986 | Clark et al. | |
| 4,633,863 A | 1/1987 | Filips et al. | |
| 4,637,819 A | 1/1987 | Oullette et al. | |
| 4,640,688 A | 2/1987 | Hauser | 604/352 |
| 4,641,643 A | 2/1987 | Greer | |
| 4,645,492 A | 2/1987 | Weeks | |
| 4,655,210 A | 4/1987 | Edenbaum et al. | |
| 4,655,754 A * | 4/1987 | Richmond et al. | 604/323 |
| 4,661,093 A | 4/1987 | Beck et al. | |
| 4,664,652 A | 5/1987 | Weilbacher | |
| 4,664,662 A | 5/1987 | Webster | |
| 4,667,666 A | 5/1987 | Frysliie | |
| 4,679,590 A | 7/1987 | Hergenroeder | |
| 4,704,102 A | 11/1987 | Guthery | 604/28 |
| 4,710,165 A | 12/1987 | McNeil et al. | 604/67 |
| 4,713,051 A | 12/1987 | Steppe et al. | 604/30 |
| 4,717,332 A | 1/1988 | Edens | 431/8 |
| 4,717,379 A | 1/1988 | Ekholmer | 604/43 |
| 4,717,382 A | 1/1988 | Clemens et al. | |
| 4,733,659 A | 3/1988 | Edenbaum et al. | |
| 4,735,606 A | 4/1988 | Davison | |
| 4,735,610 A | 4/1988 | Akkas et al. | |
| 4,737,148 A | 4/1988 | Blake | 604/126 |
| 4,740,202 A | 4/1988 | Stacey et al. | |
| 4,743,232 A | 5/1988 | Kruger | |
| 4,747,166 A | 5/1988 | Kuntz | |
| 4,758,220 A | 7/1988 | Sundblom et al. | 604/65 |
| 4,759,354 A | 7/1988 | Quarfoot | |
| 4,765,316 A | 8/1988 | Marshall | |
| 4,778,446 A | 10/1988 | Jensen | |
| 4,778,456 A | 10/1988 | Lokken | |
| 4,787,888 A | 11/1988 | Fox | 604/20 |
| 4,798,578 A | 1/1989 | Ranford | |
| 4,820,265 A | 4/1989 | DeSatnick et al. | |
| 4,820,284 A | 4/1989 | Hauri | |
| 4,826,494 A * | 5/1989 | Richmond et al. | 604/323 |
| 4,826,949 A | 5/1989 | Stanko | 528/272 |
| 4,834,110 A | 5/1989 | Richard | |
| 4,838,883 A | 6/1989 | Matsuura | 604/349 |
| 4,840,187 A | 6/1989 | Brazier | 128/844 |
| 4,841,962 A | 6/1989 | Berg et al. | 128/156 |
| 4,850,350 A | 7/1989 | Jackson | 128/207.16 |
| 4,863,449 A | 9/1989 | Therriault et al. | 604/352 |
| 4,872,450 A | 10/1989 | Austad | |
| 4,878,901 A | 11/1989 | Sachse | 604/174 |
| 4,890,608 A | 1/1990 | Steer | |
| 4,897,081 A | 1/1990 | Poirier et al. | |
| 4,900,302 A * | 2/1990 | Newton | 604/30 |
| 4,902,508 A | 2/1990 | Badylak et al. | 424/95 |
| 4,906,233 A | 3/1990 | Moriuchi et al. | 604/174 |
| 4,906,240 A | 3/1990 | Reed et al. | |
| 4,915,694 A | 4/1990 | Yamamoto et al. | |
| 4,917,112 A | 4/1990 | Kalt | |
| 4,919,654 A | 4/1990 | Kalt | 604/180 |
| 4,921,492 A | 5/1990 | Schultz et al. | |
| 4,930,997 A | 6/1990 | Bennett | |
| 4,941,882 A | 7/1990 | Ward et al. | |
| 4,950,230 A | 8/1990 | Kendell | 604/28 |

| | | | |
|---|---|---|---|
| 4,953,565 A | 9/1990 | Tachibana et al. | |
| 4,956,178 A | 9/1990 | Badylak et al. ............... 424/551 | |
| 4,957,492 A | 9/1990 | McVay | |
| 4,962,761 A | 10/1990 | Golden | |
| 4,969,880 A | 11/1990 | Zamierowski | |
| 4,969,881 A | 11/1990 | Viesturs | |
| 4,970,298 A | 11/1990 | Silver et al. .................. 530/356 | |
| 4,985,019 A | 1/1991 | Michelson .................... 604/180 | |
| 4,988,336 A | 1/1991 | Kohn | |
| 4,990,144 A | 2/1991 | Blott | |
| 4,991,574 A | 2/1991 | Pocknell | |
| 4,994,022 A | 2/1991 | Steffler et al. | |
| 4,997,425 A | 3/1991 | Shioya et al. | |
| 5,000,172 A | 3/1991 | Ward | |
| 5,000,741 A | 3/1991 | Kalt | |
| 5,002,528 A | 3/1991 | Palestrant | |
| 5,002,529 A | 3/1991 | Cunningham | |
| 5,003,971 A | 4/1991 | Buckley | |
| 5,014,389 A | 5/1991 | Ogilvie et al. | |
| 5,034,003 A | 7/1991 | Denance | |
| 5,034,006 A | 7/1991 | Hosoda et al. | |
| 5,035,865 A | 7/1991 | Inaba et al. | |
| 5,037,397 A | 8/1991 | Kalt et al. ..................... 604/174 | |
| 5,042,978 A | 8/1991 | Quenin et al. | |
| 5,045,777 A | 9/1991 | Itagaki | |
| 5,060,662 A | 10/1991 | Farnsworth, III | |
| 5,071,409 A | 12/1991 | Rosenberg | |
| 5,073,172 A | 12/1991 | Fell | |
| 5,080,650 A | 1/1992 | Hirsch et al. .................. 604/104 | |
| 5,086,170 A | 2/1992 | Luheshi et al. ............... 540/303 | |
| 5,086,763 A | 2/1992 | Hathman | |
| 5,086,764 A | 2/1992 | Gilman | |
| 5,092,858 A | 3/1992 | Benson et al. ................. 604/319 | |
| 5,100,395 A | 3/1992 | Rosenberg .................... 604/284 | |
| 5,100,396 A | 3/1992 | Zamierowski | |
| 5,101,808 A | 4/1992 | Kobayashi et al. | |
| 5,106,362 A | 4/1992 | Gilman | |
| 5,106,629 A | 4/1992 | Cartmell et al. | |
| 5,108,364 A | 4/1992 | Takezawa et al. ............. 604/43 | |
| 5,134,994 A | 8/1992 | Say ........................... 128/200.24 | |
| 5,135,518 A | 8/1992 | Vera | |
| 5,146,925 A | 9/1992 | Snow | |
| 5,147,338 A | 9/1992 | Lang et al. | |
| 5,149,331 A | 9/1992 | Ferdman et al. | |
| 5,152,757 A | 10/1992 | Eriksson | |
| 5,160,322 A | 11/1992 | Scheremet et al. | |
| 5,167,613 A | 12/1992 | Karami et al. | |
| 5,167,622 A | 12/1992 | Muto .............................. 604/35 | |
| 5,170,781 A | 12/1992 | Loomis | |
| 5,176,502 A | 1/1993 | Sanderson et al. | |
| 5,176,663 A | 1/1993 | Svedman et al. | |
| 5,176,667 A | 1/1993 | DeBring | |
| 5,181,908 A | 1/1993 | Bell ................................ 604/24 | |
| 5,189,609 A | 2/1993 | Tivig et al. | |
| 5,197,948 A | 3/1993 | Ghodsian ....................... 604/30 | |
| 5,215,522 A | 6/1993 | Page et al. ...................... 604/33 | |
| 5,215,539 A | 6/1993 | Schoolman | |
| 5,224,929 A | 7/1993 | Remiszewski ................. 604/30 | |
| 5,228,431 A | 7/1993 | Giarretto | |
| 5,230,350 A | 7/1993 | Fentress | |
| 5,232,453 A | 8/1993 | Plass et al. .................... 604/180 | |
| 5,238,654 A | 8/1993 | Nohl et al. | |
| 5,249,121 A | 9/1993 | Baum et al. | |
| 5,256,418 A | 10/1993 | Kemp et al. ................... 424/423 | |
| 5,261,893 A | 11/1993 | Zamierowski | |
| 5,263,922 A | 11/1993 | Sova et al. | |
| 5,265,605 A | 11/1993 | Afflerbach | |
| 5,275,826 A | 1/1994 | Badylak et al. ............... 424/551 | |
| 5,278,100 A | 1/1994 | Doan et al. .................... 437/200 | |
| 5,279,550 A | 1/1994 | Habib et al. .................... 604/38 | |
| 5,281,422 A | 1/1994 | Badylak et al. ............... 424/551 | |
| 5,291,887 A | 3/1994 | Stanley et al. | |
| 5,298,015 A | 3/1994 | Komatsuzaki et al. | |
| 5,306,298 A | 4/1994 | Godley, III et al. | |
| 5,314,409 A | 5/1994 | Sarosiek et al. ............... 604/101 | |
| 5,330,452 A | 7/1994 | Zook | |
| 5,335,651 A * | 8/1994 | Foster et al. .............. 128/202.13 | |
| 5,338,293 A | 8/1994 | Jeppsson et al. ............... 604/29 | |
| 5,342,293 A | 8/1994 | Zanger | |
| 5,342,301 A | 8/1994 | Saab ................................. 604/96 |
| 5,342,376 A | 8/1994 | Ruff ................................ 606/151 |
| 5,344,415 A | 9/1994 | DeBusk et al. |
| 5,349,965 A | 9/1994 | McCarver |
| 5,352,463 A | 10/1994 | Badylak et al. ............... 424/551 |
| 5,358,494 A | 10/1994 | Svedman |
| 5,370,610 A | 12/1994 | Reynolds ........................ 604/43 |
| 5,372,821 A | 12/1994 | Badylak et al. ............... 424/551 |
| 5,374,254 A | 12/1994 | Buma |
| 5,376,252 A | 12/1994 | Ekstrom et al. |
| 5,380,280 A | 1/1995 | Peterson |
| 5,395,315 A | 3/1995 | Griep |
| 5,409,013 A | 4/1995 | Clement ........................ 128/753 |
| 5,413,788 A | 5/1995 | Edwards et al. |
| 5,419,768 A | 5/1995 | Kayser |
| 5,431,622 A | 7/1995 | Pyrozyk et al. |
| 5,437,622 A | 8/1995 | Carion ............................ 602/57 |
| 5,437,651 A | 8/1995 | Todd et al. |
| 5,439,452 A | 8/1995 | McCarty ........................ 604/248 |
| 5,445,604 A | 8/1995 | Lang |
| 5,445,833 A | 8/1995 | Badylak et al. ............... 424/551 |
| 5,447,505 A | 9/1995 | Valentine et al. |
| 5,449,383 A | 9/1995 | Chatelier et al. .................. 623/1 |
| 5,451,215 A | 9/1995 | Wolter |
| 5,451,373 A | 9/1995 | Lewis et al. |
| 5,478,333 A | 12/1995 | Asherman, Jr. |
| 5,484,420 A | 1/1996 | Russo |
| 5,484,427 A | 1/1996 | Gibbons |
| 5,484,428 A | 1/1996 | Drainville et al. |
| 5,487,889 A | 1/1996 | Eckert et al. |
| 5,516,533 A | 5/1996 | Badylak et al. ............... 424/551 |
| 5,520,652 A | 5/1996 | Peterson |
| 5,527,293 A | 6/1996 | Zamierowski |
| 5,531,670 A | 7/1996 | Westby et al. |
| 5,533,981 A | 7/1996 | Mandro et al. |
| 5,534,346 A | 7/1996 | Robinson |
| 5,540,668 A | 7/1996 | Wilson et al. ................. 604/248 |
| 5,542,918 A | 8/1996 | Atkinson |
| 5,549,584 A | 8/1996 | Gross |
| 5,554,389 A | 9/1996 | Badylak et al. ............... 424/558 |
| 5,556,375 A | 9/1996 | Ewall |
| 5,558,639 A | 9/1996 | Gangemi et al. |
| 5,573,784 A | 11/1996 | Badylak et al. ............... 424/551 |
| 5,578,022 A | 11/1996 | Scherson et al. |
| 5,578,662 A | 11/1996 | Bennett et al. ................... 524/54 |
| 5,607,388 A | 3/1997 | Ewall |
| 5,621,035 A | 4/1997 | Lyles et al. .................... 524/404 |
| 5,624,418 A | 4/1997 | Shepard |
| 5,628,735 A | 5/1997 | Skow |
| 5,629,186 A | 5/1997 | Yasukawa et al. ............. 435/177 |
| 5,631,011 A | 5/1997 | Wadström ..................... 424/400 |
| 5,635,201 A | 6/1997 | Fabo |
| 5,636,643 A * | 6/1997 | Argenta et al. ................ 128/897 |
| 5,641,518 A | 6/1997 | Badylak et al. ............... 424/551 |
| 5,645,081 A | 7/1997 | Argenta et al. |
| 5,645,860 A | 7/1997 | Knapp et al. .................. 424/551 |
| 5,655,258 A | 8/1997 | Heintz |
| 5,656,027 A | 8/1997 | Ellingboe |
| 5,662,598 A | 9/1997 | Tobin |
| 5,662,624 A | 9/1997 | Sundstrom et al. |
| 5,662,625 A | 9/1997 | Westwood |
| 5,669,892 A | 9/1997 | Keogh et al. |
| 5,672,151 A | 9/1997 | Calderon-Garciadueñas ... 602/21 |
| 5,672,152 A | 9/1997 | Mason et al. |
| 5,674,193 A | 10/1997 | Hayes |
| 5,678,564 A | 10/1997 | Lawrence et al. |
| 5,681,290 A | 10/1997 | Alexander ..................... 604/180 |
| 5,690,815 A | 11/1997 | Krasnoff et al. |
| 5,695,998 A | 12/1997 | Badylak et al. ............... 435/391 |
| 5,697,920 A | 12/1997 | Gibbons |
| 5,711,969 A | 1/1998 | Patel et al. ..................... 424/551 |
| 5,718,955 A | 2/1998 | McGuire et al. |
| 5,735,833 A | 4/1998 | Olson |
| 5,738,656 A * | 4/1998 | Wagner ......................... 604/119 |
| 5,741,237 A * | 4/1998 | Walker .......................... 604/317 |
| 5,749,842 A | 5/1998 | Cheong et al. .................. 602/41 |
| 5,753,267 A | 5/1998 | Badylak et al. ............... 424/551 |
| 5,755,791 A | 5/1998 | Whitson et al. ................. 623/15 |
| 5,759,570 A | 6/1998 | Arnold |

| | | |
|---|---|---|
| 5,762,640 A | 6/1998 | Kajiwara et al. |
| 5,762,966 A | 6/1998 | Knapp et al. ............... 424/551 |
| 5,780,281 A | 7/1998 | Yasukawa et al. ........... 435/176 |
| 5,782,871 A | 7/1998 | Fujiwara et al. |
| 5,795,584 A | 8/1998 | Totakura et al. ............ 424/426 |
| 5,800,383 A | 9/1998 | Chandler et al. ............... 604/35 |
| 5,817,145 A | 10/1998 | Augustine et al. |
| 5,827,246 A | 10/1998 | Bowen |
| 5,827,296 A | 10/1998 | Morris et al. |
| 5,855,619 A | 1/1999 | Caplan et al. .................. 623/11 |
| 5,866,414 A | 2/1999 | Badylak et al. ............. 435/325 |
| 5,881,723 A | 3/1999 | Wallace et al. |
| 5,891,111 A | 4/1999 | Ismael ......................... 604/280 |
| 5,902,874 A | 5/1999 | Roby et al. .................... 528/310 |
| 5,902,875 A | 5/1999 | Roby et al. .................... 528/310 |
| 5,911,222 A | 6/1999 | Lawrence et al. |
| 5,914,387 A | 6/1999 | Roby et al. .................... 528/310 |
| 5,919,476 A | 7/1999 | Fischer et al. |
| 5,921,972 A | 7/1999 | Skow |
| 5,928,174 A | 7/1999 | Gibbins |
| 5,931,304 A | 8/1999 | Hammond ................... 206/570 |
| 5,941,859 A | 8/1999 | Lerman |
| 5,942,496 A | 8/1999 | Bonadio et al. ................ 514/44 |
| 5,947,914 A | 9/1999 | Augustine |
| 5,951,295 A | 9/1999 | Lyles et al. ................ 433/228.1 |
| 5,954,680 A | 9/1999 | Augustine |
| 5,961,480 A | 10/1999 | Augustine |
| 5,962,427 A | 10/1999 | Goldstein et al. ............... 514/44 |
| 5,964,721 A | 10/1999 | Augustine |
| 5,964,723 A | 10/1999 | Augustine |
| 5,986,163 A | 11/1999 | Augustine |
| 5,997,568 A | 12/1999 | Liu ............................... 606/228 |
| 6,010,527 A | 1/2000 | Augustine et al. |
| 6,013,048 A | 1/2000 | Podany et al. .................. 604/22 |
| 6,017,493 A | 1/2000 | Cambron et al. |
| 6,039,724 A | 3/2000 | Seifert et al. |
| 6,045,518 A | 4/2000 | Augustine |
| 6,045,541 A | 4/2000 | Matsumoto et al. |
| 6,051,747 A | 4/2000 | Lindqvist et al. |
| 6,056,730 A | 5/2000 | Greter |
| 6,071,254 A | 6/2000 | Augustine |
| 6,071,267 A | 6/2000 | Zamierowski |
| 6,071,304 A | 6/2000 | Augustine et al. |
| 6,080,189 A | 6/2000 | Augustine et al. |
| 6,080,243 A | 6/2000 | Insley et al. |
| 6,093,160 A | 7/2000 | Augustine et al. |
| 6,093,230 A | 7/2000 | Johnson, III et al. |
| 6,095,992 A | 8/2000 | Augustine |
| 6,099,567 A | 8/2000 | Badylak et al. ................. 623/13 |
| 6,110,197 A | 8/2000 | Augustine et al. |
| 6,113,561 A | 9/2000 | Augustine |
| 6,117,111 A | 9/2000 | Fleischmann |
| 6,135,116 A | 10/2000 | Vogel et al. |
| 6,142,982 A | 11/2000 | Hunt et al. |
| 6,143,945 A | 11/2000 | Augustine et al. |
| 6,149,614 A | 11/2000 | Dunshee et al. |
| 6,171,344 B1 | 1/2001 | Atala ......................... 623/23.64 |
| 6,174,306 B1 | 1/2001 | Fleischmann |
| 6,203,563 B1 | 3/2001 | Fernandez |
| 6,206,931 B1 | 3/2001 | Cook et al. ................. 623/23.75 |
| 6,207,875 B1 | 3/2001 | Lindqvist et al. |
| 6,213,965 B1 | 4/2001 | Augustine et al. |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine et al. |
| 6,241,697 B1 | 6/2001 | Augustine |
| 6,241,698 B1 | 6/2001 | Augustine |
| 6,241,747 B1 | 6/2001 | Ruff ............................. 606/216 |
| 6,244,311 B1 | 6/2001 | Hand et al. |
| 6,244,698 B1 | 6/2001 | Chino et al. |
| 6,248,084 B1 | 6/2001 | Augustine et al. |
| 6,254,557 B1 | 7/2001 | Augustine et al. |
| 6,254,580 B1 | 7/2001 | Svedman |
| 6,259,067 B1 | 7/2001 | Faries, Jr. et al. |
| 6,264,622 B1 | 7/2001 | Augustine |
| 6,264,979 B1 | 7/2001 | Svedman |
| 6,267,740 B1 | 7/2001 | Augustine et al. |
| 6,283,931 B1 | 9/2001 | Augustine |
| 6,284,941 B1 | 9/2001 | Cox et al. |
| 6,287,316 B1 | 9/2001 | Agarwal et al. ............... 606/151 |
| 6,290,685 B1 | 9/2001 | Insley et al. |
| 6,293,917 B1 | 9/2001 | Augustine et al. |
| 6,325,798 B1 | 12/2001 | Edwards et al. ................. 606/41 |
| 6,345,623 B1 | 2/2002 | Heaton et al. |
| 6,364,853 B1 | 4/2002 | French et al. ................... 604/35 |
| 6,394,142 B1 | 5/2002 | Woelfel et al. ................ 138/115 |
| 6,398,767 B1 | 6/2002 | Fleischmann |
| 6,410,427 B1 | 6/2002 | Hu ................................. 438/655 |
| 6,440,427 B1 | 8/2002 | Wadström ..................... 424/400 |
| 6,458,109 B1 | 10/2002 | Henley et al. |
| 6,471,685 B1 | 10/2002 | Johnson |
| 6,472,581 B1 | 10/2002 | Muramatsu et al. |
| 6,488,643 B1 | 12/2002 | Tumey et al. ................... 602/13 |
| 6,491,682 B2 | 12/2002 | Paderni |
| 6,491,693 B1 | 12/2002 | Lytinas |
| 6,493,568 B1 | 12/2002 | Bell et al. ...................... 600/323 |
| 6,500,112 B1 | 12/2002 | Khouri |
| 6,520,982 B1 | 2/2003 | Boynton et al. |
| 6,553,998 B2 | 4/2003 | Heaton et al. |
| 6,557,704 B1 | 5/2003 | Randolph |
| 6,559,773 B1 | 5/2003 | Berry |
| 6,599,277 B2 | 7/2003 | Neubert |
| 6,626,891 B2 | 9/2003 | Ohmstede |
| 6,638,270 B2 | 10/2003 | Johnson |
| 6,648,862 B2 | 11/2003 | Watson |
| 6,663,349 B1 | 12/2003 | Discenzo et al. |
| 6,685,681 B2 | 2/2004 | Lockwood et al. |
| 6,691,047 B1 | 2/2004 | Fredericks |
| 6,695,823 B1 | 2/2004 | Lina et al. |
| 6,695,824 B2 | 2/2004 | Howard et al. |
| 6,719,779 B2 | 4/2004 | Daoud |
| 6,749,592 B2 | 6/2004 | Lord |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,966,889 B2 | 11/2005 | Saab ........................... 604/96.01 |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,735 B2 | 10/2006 | Weston ......................... 604/543 |
| 7,144,390 B1 | 12/2006 | Hannigan et al. |
| 7,195,624 B2 | 3/2007 | Lockwood et al. |
| 7,245,291 B2 | 7/2007 | Sharif et al. .................... 345/172 |
| 7,276,051 B1 | 10/2007 | Henley et al. |
| 7,338,482 B2 | 3/2008 | Lockwood et al. ............ 604/543 |
| 7,381,211 B2 | 6/2008 | Zamierowski ................ 606/215 |
| 7,422,576 B2 | 9/2008 | Boynton et al. ............... 607/104 |
| 7,524,286 B2 | 4/2009 | Johnson ......................... 600/309 |
| 7,534,927 B2 | 5/2009 | Lockwood et al. ............ 602/46 |
| 2001/0029956 A1 | 10/2001 | Argenta et al. |
| 2001/0034499 A1 | 10/2001 | Sessions |
| 2001/0043943 A1 | 11/2001 | Coffey |
| 2001/0052681 A1 | 12/2001 | Deavila ....................... 280/47.19 |
| 2002/0065494 A1 | 5/2002 | Lockwood et al. |
| 2002/0077661 A1 | 6/2002 | Saadat ........................... 606/221 |
| 2002/0082567 A1 | 6/2002 | Lockwood et al. ............ 604/313 |
| 2002/0082668 A1 | 6/2002 | Ingman |
| 2002/0085952 A1 | 7/2002 | Ellingboe et al. ................ 422/45 |
| 2002/0115951 A1 | 8/2002 | Norstrem et al. ................ 602/27 |
| 2002/0115952 A1 | 8/2002 | Johnson et al. |
| 2002/0120185 A1 | 8/2002 | Johnson ......................... 600/345 |
| 2002/0143286 A1 | 10/2002 | Tumey |
| 2002/0161317 A1 | 10/2002 | Risk et al. |
| 2002/0183702 A1 | 12/2002 | Henley et al. .................. 604/305 |

| | | | | | |
|---|---|---|---|---|---|
| 2002/0193723 A1 | 12/2002 | Batdorf, Sr. et al. | EP | 0853 950 A1 | 7/1998 |
| 2003/0032951 A1 | 2/2003 | Rittman, III et al. | EP | 0853950 A1 | 7/1998 |
| 2003/0077311 A1 | 4/2003 | Vyakarnam et al. ............ 435/41 | EP | 0777504 B1 | 10/1998 |
| 2003/0093041 A1 | 5/2003 | Risk et al. | EP | 0880953 A2 | 12/1998 |
| 2003/0143352 A1 | 7/2003 | Yang et al. .................. 428/36.9 | EP | 1088569 A2 | 4/2001 |
| 2003/0208149 A1 | 11/2003 | Coffey | EP | 1100574 | 5/2001 |
| 2003/0219469 A1 | 11/2003 | Johnson et al. | EP | 1 190 732 A1 | 3/2002 |
| 2003/0225441 A1 | 12/2003 | Boynton et al. | EP | 1 018 967 B1 | 8/2004 |
| 2004/0030304 A1 | 2/2004 | Hunt et al. | EP | 1726 276 A2 | 11/2006 |
| 2004/0039415 A1 | 2/2004 | Zamierowski | FR | 500253 | 3/1920 |
| 2004/0064111 A1 | 4/2004 | Lockwood et al. | FR | 1303238 | 7/1962 |
| 2004/0167482 A1 | 8/2004 | Watson | GB | 3090 | 6/1902 |
| 2004/0225208 A1 | 11/2004 | Johnson | GB | 641061 | 8/1950 |
| 2004/0243073 A1 | 12/2004 | Lockwood et al. | GB | 692578 | 6/1953 |
| 2004/0249353 A1 | 12/2004 | Risks, Jr. et al. | GB | 1549756 | 8/1979 |
| 2004/0260230 A1 | 12/2004 | Randolph | GB | 1584772 | 2/1981 |
| 2005/0004534 A1 | 1/2005 | Lockwood et al. | GB | 2195255 A | 4/1988 |
| 2005/0010153 A1 | 1/2005 | Lockwood et al. | GB | 2197789 A | 6/1988 |
| 2005/0033197 A1 | 2/2005 | Cottler | GB | 2220357 A | 1/1990 |
| 2005/0065484 A1 | 3/2005 | Watson, Jr. | GB | 2235877 A | 3/1991 |
| 2005/0070858 A1 | 3/2005 | Lockwood et al. | GB | 2307180 A | 5/1997 |
| 2005/0085795 A1 | 4/2005 | Lockwood et al. | GB | 2329127 A | 3/1999 |
| 2005/0090787 A1 | 4/2005 | Risk, Jr. et al. | GB | 2333965 A | 8/1999 |
| 2005/0131327 A1 | 6/2005 | Lockwood et al. | GB | 2336546 A | 10/1999 |
| 2005/0177190 A1 | 8/2005 | Zamierowski | GB | 2336546 A | 10/1999 |
| 2005/0182445 A1 | 8/2005 | Zamierowski | GB | 2342584 A | 4/2000 |
| 2005/0182446 A1 | 8/2005 | DeSantis ....................... 606/222 | GB | 2344531 A | 6/2000 |
| 2005/0234485 A1 | 10/2005 | Seegert et al. | GB | 2351025 A | 12/2000 |
| 2005/0234510 A1 | 10/2005 | Zamierowski | GB | 2356148 | 5/2001 |
| 2005/0240220 A1 | 10/2005 | Zamierowski | HU | 199304 B | 1/1989 |
| 2005/0283105 A1 | 12/2005 | Heaton et al. | HU | 51150 | 4/1990 |
| 2006/0015087 A1 | 1/2006 | Risk, Jr. et al. | HU | 205557 B | 4/1990 |
| 2006/0029650 A1 | 2/2006 | Coffey | HU | P9006526 | 1/1993 |
| 2006/0029675 A1 | 2/2006 | Ginther | HU | P9302966 | 7/1996 |
| 2006/0041247 A1 | 2/2006 | Petrosenko et al. | HU | 76351 | 8/1997 |
| 2006/0079852 A1 | 4/2006 | Bubb et al. | HU | 215563 B | 8/1997 |
| 2006/0129137 A1 | 6/2006 | Lockwood et al. | HU | 1666 | 12/1999 |
| 2006/0149170 A1 | 7/2006 | Boynton et al. | JP | 57-177758 | 11/1982 |
| 2006/0149171 A1 | 7/2006 | Vogel et al. | JP | 4-129536 | 4/1992 |
| 2006/0173253 A1 | 8/2006 | Ganapathy et al. | JP | 06327761 | 11/1994 |
| 2006/0189910 A1 | 8/2006 | Johnson et al. | SE | 84485 | 10/1935 |
| 2006/0213527 A1 | 9/2006 | Argenta et al. | SG | 71559 | 4/2002 |
| 2007/0005028 A1 | 1/2007 | Risk, Jr. et al. | SU | 587941 | 1/1978 |
| 2007/0014837 A1 | 1/2007 | Johnson et al. | SU | 1268175 A1 | 11/1986 |
| 2007/0021697 A1 | 1/2007 | Ginther et al. | WO | WO 80/02182 | 10/1980 |
| 2007/0021698 A1 | 1/2007 | Fleischmann | WO | WO 87/04626 | 8/1987 |
| 2007/0032778 A1 | 2/2007 | Heaton et al. | WO | WO 89/04158 | 5/1989 |
| 2007/0038172 A1 | 2/2007 | Zamierowski | WO | WO 90/10424 | 9/1990 |
| 2007/0156104 A1 | 7/2007 | Lockwood et al. | WO | WO 90/11795 | 10/1990 |
| 2007/0233022 A1 | 10/2007 | Henley et al. .................. 604/304 | WO | WO 91/00718 | 1/1991 |
| 2009/0082740 A1 | 3/2009 | Lockwood et al. ............. 602/41 | WO | WO9108793 | 6/1991 |
| 2010/0063483 A1 | 3/2010 | Adahan .......................... 604/543 | WO | WO 91/16030 | 10/1991 |
| | | | WO | WO9212750 | 8/1992 |
| FOREIGN PATENT DOCUMENTS | | | WO | WO 92/19313 | 11/1992 |
| AU | 745271 | 4/1999 | WO | WO 92/20299 | 11/1992 |
| AU | 755496 | 2/2002 | WO | WO93/09715 | 3/1993 |
| CA | 1127488 | 7/1982 | WO | WO 93/09727 | 5/1993 |
| CA | 2005436 | 6/1990 | WO | WO 94/00090 | 1/1994 |
| CA | 2303085 | 9/1997 | WO | WO 94/20041 | 9/1994 |
| DE | 032727 | 3/1923 | WO | WO 96/05873 | 2/1996 |
| DE | 2640413 A1 | 3/1978 | WO | WO 9605873 A1 * | 2/1996 |
| DE | 28 09 828 A1 | 9/1978 | WO | WO 96/15745 | 5/1996 |
| DE | 3102674 A1 | 9/1982 | WO | WO 97/18007 | 5/1997 |
| DE | 3539533 A1 | 5/1987 | WO | WO 98/02205 | 1/1998 |
| DE | 40 12 232 | 10/1991 | WO | WO 98/38944 | 9/1998 |
| DE | 4111122 A1 | 4/1993 | WO | WO 99/01173 | 1/1999 |
| DE | 4306478 A1 | 9/1994 | WO | WO 99/13793 | 3/1999 |
| DE | 29504378 U1 | 10/1995 | WO | WO99/23990 | 5/1999 |
| DE | 29715634 | 11/1997 | WO | WO 99/59816 | 11/1999 |
| DE | 19722075 C1 | 10/1998 | WO | WO 00/07653 | 2/2000 |
| DK | 64055 | 10/1945 | WO | WO 0007653 A1 * | 2/2000 |
| EP | 0 100 148 A1 | 2/1984 | WO | WO 00/15277 | 3/2000 |
| EP | 0117632 A2 | 9/1984 | WO | WO 00/21586 | 4/2000 |
| EP | 0 161 865 A2 | 11/1985 | WO | WO 0021586 A1 * | 4/2000 |
| EP | 0 358 302 A2 | 3/1990 | WO | WO 00/26100 | 5/2000 |
| EP | 0424165 A1 | 4/1991 | WO | WO 00/28890 | 5/2000 |
| EP | 0485657 A1 | 5/1992 | WO | WO 00/30567 | 6/2000 |
| EP | 0547496 A1 | 6/1993 | WO | WO 00/32247 | 6/2000 |
| EP | 0800953 A2 | 2/1998 | WO | WO 00/38552 | 7/2000 |

| | | |
|---|---|---|
| WO | WO 00/38755 | 7/2000 |
| WO | WO 00/42958 | 7/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 A1 | 5/2001 |
| WO | WO 01/37922 A2 | 5/2001 |
| WO | WO 01/49233 A1 | 7/2001 |
| WO | WO 01/85248 | 11/2001 |
| WO | WO 01/85248 A1 | 11/2001 |
| WO | WO 01/89431 | 11/2001 |
| WO | WO02/38091 | 5/2002 |
| WO | WO 02/43634 | 6/2002 |
| WO | WO 03/005943 A3 | 1/2003 |
| WO | WO 03/045492 A1 | 6/2003 |
| WO | WO 03/057071 | 7/2003 |
| WO | WO 03/057307 | 7/2003 |
| WO | WO 03/101508 | 12/2003 |

OTHER PUBLICATIONS

Oosterbroek, R.E et al, "A Micromachined Pressure/Flow-sensor" (Abstract only), http://www.ingentaconnect.com/content/els/09244247/1999/00000077/00000003/art00188, Sensors and Actuators A: vol. 77, No. 3, Nov. 2, 1999.*

Oosterbroek et al.*

Davydov, et al., Vestn. Khir., Sep. 1988—"Vacuum Therapy in the Treatment of Acute Suppurative Diseases of Soft Tissues and Suppurative Wounds"—(English translation by R. McElroy Translation Co., Austin, Texas).

Davydov, et al., Khirurgiia, Jun. 1990—"Pathogenic Mechanism of the Effect of Vacuum Therapy on the Course of the Wound Process" (English translation by R. McElroy Translation Co., Austin, Texas).

Davydov, et al., Vestn. Khir., Nov. 1986—"Vacuum Therapy in the Treatment of Suppurative Lactation Mastitis" (English translation by R. McElroy Translation Co., Austin, Texas).

Davydov, et al., Vestn. Khir., Oct. 1988—"Bacteriological and Cytological Evaluation of the Vacuum Therapy of Suppurative Wounds" (English translation by R. McElroy Translation Co., Austin, Texas).

Davydov, et al., Vestn. Khir., Mar. 1990—"Basis of the Use of Forced Early Secondary Suture in the Treatment of Suppurative Wounds" (English translation by R. McElroy Translation Co., Austin, Texas).

Mirazimov, et al., Ortop Travmatol Protez., Oct. 1966—"Free Skin Graft of the Foot with Preparation of the Wound Surface by Vacuum Treatment" (English translation by R. McElroy Translation Co., Austin, Texas).

Borzov, et al., Vestn. Dermatol. Venerol., Aug. 1965—"Vacuum Therapy of Some Skin Diseases" (English translation by R. McElroy Translation Co., Austin, Texas).

Jeter, et al., Chronic Wound Care; 27: pp. 240-246—"Managing Draining Wounds and Fistulae: New and Established Methods".

Mulder, et al., Wound Healing Publications 1991—"Clinicians' Pocket Guide to Chronic Wound Repair".

Valenta, AIN Apr. 1994; pp. 44-45—"Using the Vacuum Dressing Alternative for Difficult Wounds".

Wolthuis, et al., Physiological Reviews Jul. 1974; vol. 54, No. 3, pp. 566-595—"Physiological Effects of Locally Applied Reduced Pressure in Man".

Fleischmann—WundForum Spezial IHA 1994; pp. 54-55—"Vacuum Sealing for Treatment of Problematical Wounds" (English translation provided).

Dunlop, et al., Br. J. Surg. May 1990; vol. 77: pp. 562-563—"Vacuum Drainage of Groin Wounds after Vascular Surgery: A Controlled Trial".

Comment-Dunlop et al., Apr. 1991, pp. 505-506 on "Vacuum Drainage of Groin Wounds after Vascular Surgery".

Landis, et al., Alternate Suction and Pressure, pp. 925-961—"The Effects of Alternate Suction and Pressure on Blood Flow to the Lower Extremities".

Morykwas, et al., Extracellular Matric and Healing 1993, pp. 800—"Use of Negative Pressure to Increase the Rate of Granulation Tissue Formation in Chronic Open Wounds".

Svedman, et al., Annals of Plastic Surgery Aug. 1986; vol. 17, No. 2: pp. 125-133—"A Dressing System Providing Fluid Supply and Suction Drainage Used for Continuous or Intermittent Irrigation".

Schneider, et al., Plastic and Reconstructive Surgery Sep. 1998, pp. 1195-1198—"A New and Reliable Method of Securing Skin Grafts to the Difficult Recipient Bed".

Morykwas, et al., www.sma.org/soa/jsoawt97—"Nonsurgical Modalities to Enhance Healing and Care of Soft Tissue Wounds".

Chariker, et al., Contemporary Surgery Jun. 1989; vol. 34: pp. 59-63—"Effective Management of Incisional and Cutaneous Fistulae with Closed Suction Wound Drainage".

Tittel, Eingag and Annahme des Manuskripts, Jan. 7, 1987, pp. 104-107—"New Standards in Postoperative Wound Drainage".

Genecov, et al., Annals of Plastic Surgery Mar. 1998, vol. 40, No. 3: pp. 219-225—"A Controlled Sub-atmospheric Pressure Dressing Increases the Rate of Skin Graft Donor Site Reepithelialization".

Morykwas, et al., Annals of Plastic Surgery Jun. 1997; vol. 38, No. 6—"Vacuum-Assisted Closure: A New Method for Wound Control and Treatment: Animal Studies and Basic Foundation".

Argenta, et al., Annals of Plastic Surgery Jun. 1997; vol. 38, No. 6—"Vacuum-Assisted Closure: A New Method for Wound Control and Treatment: Clinical Experience".

Medical Industry Week—article "KCI Offers New Treatment for Non-Healing Wounds".

Sames, Br. Med. J. Nov. 5, 1977; vol. 2, No. 6096: 1123—"Sealing of Wounds with Vacuum Drainage".

Fleishmann, et al., Unfallchirurg, 1993; 96:488-492—"Vacuum Sealing for Treatment of Soft Tissue Injury in Open Fractures" (English translation of the Summary provided).

Teder, et al., J. of Invest. Surg. 1990; vol. 3: pp. 399-407—"Continuous Wound Irrigation in the Pig".

Kostluchenok et al., Vestn. Khir. Sep. 1986—"Vacuum Treatment in the Surgical Treatment of Suppurative Wounds" (English translation by R. McElroy Translation Co., Austin, Texas).

Lundvall, et al., Acta. Physiol. Scand. 1989; vol. 136: pp. 403-409—"Transmission of Externally Applied Negative Pressure to the Underlying Tissue. A Study on the Upper Arm of Man".

Brochure—Aeros—Instavac Aspirator.

Brochure—Pleur-Evac Adult-Pediatric—Non-Metered Disposable "3-Bottle" Unit, A-4000.

Brochure—Hiblow Air Pump.

Brochure—Aeros—Care-E-Vac.

Brochure—Acros—Moblvacll.

Brochure/Instruction Manual—Creative Medical Laboratories, Inc.—TUGS (Transportable Universal Gradient Suction) System.

Brochure—Wells Johnson Company—Point 5 Aspirator.

Brochure—Microtek Heritage, Inc.—The Wound Evac ET, Closed Wound Suction System.

Brochure—KCI—The V.A.C. (Vacuum Assisted Closure).

Brochure—Series 55—Emerson Post-Operative Suction Pumps.

Brochure—Emerson Transport Suction Unit.

Bucalo, et al., Wound Repair and Regeneration; Jul.-Sep. 1993; pp. 181-186—"Inhibition of Cell Proliferation by Chronic Wound Fluid".

Olenius, et al., Plastic and Reconstructive Surgery Feb. 1993: pp. 213-215—"Mitotic Activity in Expanded Human Skin".

Viljanto, et al., Br. J. Surg. 1976; vol. 63: pp. 427-430—"Local Hyperalimentation of Open Wounds".

Patent Application and Drawings—"Method of Treating Tissue Damage and Apparatus for Same", consisting of 28 pages.

Patent Application and Drawings—"The Enhancement of Wound Healing and Flap Survival by a New Negative Pressure Device", Argenta et al., consisting of 30 pages.

Nakayama, et al., Ann Plast Surg. May 1991; vol. 26, No. 5: pp. 499-502—"A New Dressing Method for Free Skin Grafting in Hands".

Nakayama, et al., Plast. Reconstr. Surg., Dec. 1990.; vol. 86, No. 6: pp. 1216-1219—"A New Method for the Dressing of Free Skin Grafts".

Wood, et al., Br. J. of Surg.1977; vol. 64: pp. 554-557—"Foam Elastomer Dressing in the Management of Open Granulating Wounds: Experience with 250 Patients".

Neumann, et al., J. of Biomed. Materials Research 1981, vol. 15: pp. 9-18—"Gelatin-Based Sprayable Foam as a Skin Substitute".
Brochure—Augustine Medical, Warm-Up Active Wound Therapy Wound Covers, 1999; 3 pages.
International Search Report for WO 03/045492 A1, Lockwood et al., Jun. 2003.
Abdullah, BJJ, JHK Coll Radiol, Feb. 21, 2001; vol. 4, pp. 272-273—"A New Method for Fixation of Drainage Catheters".
PCT International Search Report dated May 2, 2003 for PCT/US02/32221 filed Sep. 10, 2002.
U.S. Office Action dated Jun. 29, 2005 for U.S. Appl. No. 10/267,358, filed Oct. 9, 2002.
Oosterbroek, R.E. et al., "A Micromachined Pressure/Flow-sensor" (Abstract only), http://www.ingentaconnect.com/content/els/09244247/1999/00000077/00000003/art00188, Sensors and Actuators A: vol. 77, No. 3, Nov. 2, 1999.
Advisory Action issued in U.S. Appl. No. 10/885,431, mailed Dec. 8, 2009.
Advisory Action issued in U.S. Appl. No. 11/515,983, mailed Feb. 1, 2010.
Advisory Action issued in U.S. Appl. No. 11/761,066, mailed Feb. 16, 2010.
Decision on Appeal issued in U.S. Appl. No. 10/276,778, mailed Mar. 6, 2010.
Decision on Appeal issued in U.S. Appl. No. 11/242,543, mailed Mar. 5, 2010.
Office Action issued in U.S. Appl. No. 10/524,957, mailed Feb. 25, 2010.
Office Action issued in U.S. Appl. No. 10/664,535, mailed Dec. 15, 2009.
Office Action issued in U.S. Appl. No. 11/051,283, mailed Feb. 25, 2010.
Office Action issued in U.S. Appl. No. 11/515,983, mailed Nov. 2, 2009.
Office Action issued in U.S. Appl. No. 11/684,989, mailed Dec. 29, 2009.
Office Action issued in U.S. Appl. No. 11/761,066, mailed Dec. 9, 2009.
"Jump-Start Wound Healing with OASIS," *WOUNDS*, Special Supplement, 13(2):1-28, 2001.
"Oasis™ Wound Dressing," *SIS™ Technology*, pp. 1-4, Sep. 2001.
"Surgisis™ Soft-Tissue Graft," *SIS™ Technology*, pp. 1-4, Sep. 2001.
Arnljots and Svedman, "Irrigation Treatment in Split-Thickness Skin Grafting of Intractable Leg Ulcers," *Scand J. Plast Reconstr. Surg.*, 19(2):211-213, 1985.
Bagautdinov, "Variant of external vacuum aspiration in the treatment of purulent diseases of soft tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).
Blackburn II et al.; "Negative-pressure dressings as a bolster for skin grafts," *Annals of Plastic Surgery*, 40(5):453-457, 1998.
Brochure—"Cavi-Care," *Smith & Nephew*, 2000.
Brochure—Healthpoint® Oasis® Wound Matrix, *Cook Biotech Incorporated*, 2003.
Chinn and Burns, "Closed wound suction drainage," *The Journal of Foot Surgery*, 24(1):76-81, 1985.
Dattilo, Jr. et al.; "Medical textiles: application of an absorbable barbed bi-directional surgical suture"; *Journal of Textile and Apparel, Technology and Management*, 2(2):1-5, 2002.
Davydov et al., "Concepts for the clinical-biological management of the wound process in the treatment of purulent wounds by means of vacuum therapy," *Vestnik Khirurgi*, pp. 132-136 (and 8 page English translation thereof), Jul. 1980.
Egnell Minor, Instruction Book, First Edition, 300, 7502, pp. 24, Feb. 1975.
Egnell Minor: Addition to the Users Manual Concerning Overflow Protection—Concerns all Egnell Pumps, Feb. 3, 1983, pp. 2.
Fourth SIS-ECM Symposium, Phoenix, Arizona, Dec. 6-7, 2002.
Greer et al., "The use of subatmospheric pressure dressing therapy to close lymphocutaneous fistulas of the groin," *British Journal of Plastic Surgery*, 53(6):484-487, 2000.

Johnson, "An improved technique for skin graft placement using a suction drain," *Surgery, Gynecology, and Obstetrics*, 159(6):584-585, 1984.
Kinetic Concepts, Inc., Form 10-K—Annual report pursuant to section 13 or 15(d) of the Securities Exchange Act of 1934, for the fiscal year ended Dec. 31, 2006, United States Securities and Exchange Commission, pp. 1, 2, 3, 12, 13, and 14.
Klein, "Cook Incorporated forms dedicated tissue engineered products group," *PR Newswire*, 2000.
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Letsou et al., "Stimulation of adenylate cyclase activity in cultured endothelial cells subjected to cyclic stretch," *Journal of Cardiovascular Surgery*, 31:634-639, 1990.
Letter and Memo reporting Office Action issued in Mexican Application No. PA/a/2001/001124, mailed Jul. 13, 2004.
Masters, "Reliable, inexpensive and simple suction dressings," Letter to the Editor, *British Journal of Plastic Surgery*, Elsevier Science/The British Association of Plastic Surgeons, UK, 51(3):267, 1998.
McCarty, "Cook Incorporated forms dedicated tissue engineered products group," *Cook® Online, News and Media Information*, 2000.
Mendez-Eastman, "When wounds won't heal," *RN*, 61(1):20-24, 1998.
Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,390,131, mailed Jul. 20, 2007.
Office Action issued in Canadian Application No. 2,467,837, mailed May 27, 2009.
Office Action issued in Canadian Application No. 2,481,016, mailed Aug. 13, 2009.
Office Action issued in Czech Republic Application No. PV2001-497, mailed Feb. 7, 2001.
Office Action issued in European Application No. 00991498.7, mailed Dec. 17, 2003.
Office Action issued in European Application No. 00991498.7, mailed Jan. 2, 2006.
Office Action issued in European Application No. 01998292.5, mailed Feb. 18, 2005.
Office Action issued in European Application No. 01998292.5, mailed Jul. 17, 2006.
Office Action issued in European Application No. 01998292.5, mailed Sep. 12, 2008.
Office Action issued in European Application No. 02784588.2, mailed Sep. 15, 2005.
Office Action issued in European Application No. 08010957.2, mailed Apr. 8, 2009.
Office Action issued in European Application No. 99 937 799, mailed Aug. 18, 2003.
Office Action issued in Japanese Application No. 2004-508861, mailed Apr. 14, 2009, and English language translation thereof.
Office Action issued in Polish Application No. P-357 417, mailed Nov. 25, 2008; English translation.
Office Action issued in Polish Application No. P-364 754, 2006.
Office Action issued in U.S. Appl. No. 09/369,113, mailed Jan. 31, 2001.
Office Action issued in U.S. Appl. No. 09/725,352, mailed Dec. 12, 2002.
Office Action issued in U.S. Appl. No. 09/743,737, mailed Apr. 1, 2003.
Office Action issued in U.S. Appl. No. 09/743,737, mailed Aug. 11, 2006.
Office Action issued in U.S. Appl. No. 09/743,737, mailed Jun. 19, 2002.

Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/855,287, mailed Dec. 15, 2003.
Office Action issued in U.S. Appl. No. 09/855,287, mailed Jul. 14, 2005.
Office Action issued in U.S. Appl. No. 09/855,287, mailed Jun. 24, 2004.
Office Action issued in U.S. Appl. No. 09/855,287, mailed Oct. 1, 2002.
Office Action issued in U.S. Appl. No. 09/994,537, mailed Jan. 16, 2003.
Office Action issued in U.S. Appl. No. 09/994,537, mailed Jun. 30, 2003.
Office Action issued in U.S. Appl. No. 10/144,504, mailed May 14, 2004.
Office Action issued in U.S. Appl. No. 10/276,778, mailed Apr. 24, 2006.
Office Action issued in U.S. Appl. No. 10/276,778, mailed Aug. 7, 2008.
Office Action issued in U.S. Appl. No. 10/276,778, mailed Jul. 13, 2007.
Office Action issued in U.S. Appl. No. 10/276,778, mailed Mar. 22, 2007.
Office Action issued in U.S. Appl. No. 10/276,778, mailed Nov. 19, 2007.
Office Action issued in U.S. Appl. No. 10/276,778, mailed Oct. 11, 2006.
Office Action issued in U.S. Appl. No. 10/496,360, mailed Jun. 2, 2009.
Office Action issued in U.S. Appl. No. 10/496,360, mailed Jun. 12, 2006.
Office Action issued in U.S. Appl. No. 10/496,360, mailed Mar. 14, 2007.
Office Action issued in U.S. Appl. No. 10/496,360, mailed Mar. 26, 2008.
Office Action issued in U.S. Appl. No. 10/496,360, mailed Oct. 3, 2008.
Office Action issued in U.S. Appl. No. 10/496,360, mailed Oct. 5, 2006.
Office Action issued in U.S. Appl. No. 10/496,360, mailed Sep. 10, 2007.
Office Action issued in U.S. Appl. No. 10/496,623, mailed Jun. 9, 2006.
Office Action issued in U.S. Appl. No. 10/509,137, mailed Dec. 20, 2007.
Office Action issued in U.S. Appl. No. 10/509,137, mailed Jan. 10, 2007.
Office Action issued in U.S. Appl. No. 10/509,137, mailed Jun. 3, 2009.
Office Action issued in U.S. Appl. No. 10/509,137, mailed Jun. 22, 2007.
Office Action issued in U.S. Appl. No. 10/509,137, mailed Nov. 24, 2008.
Office Action issued in U.S. Appl. No. 10/524,957, mailed Apr. 11, 2007.
Office Action issued in U.S. Appl. No. 10/524,957, mailed Apr. 15, 2008.
Office Action issued in U.S. Appl. No. 10/524,957, mailed Aug. 3, 2009.
Office Action issued in U.S. Appl. No. 10/524,957, mailed Aug. 10, 2007.
Office Action issued in U.S. Appl. No. 10/524,957, mailed Sep. 30, 2008.
Office Action issued in U.S. Appl. No. 10/664,535, mailed Apr. 2, 2007.
Office Action issued in U.S. Appl. No. 10/664,535, mailed Apr. 17, 2008.
Office Action issued in U.S. Appl. No. 10/664,535, mailed Mar. 1, 2006.
Office Action issued in U.S. Appl. No. 10/664,535, mailed Oct. 16, 2006.
Office Action issued in U.S. Appl. No. 10/664,535, mailed Oct. 26, 2007.
Office Action issued in U.S. Appl. No. 10/885,431, mailed Apr. 15, 2008.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 11, 2006.
Office Action issued in U.S. Appl. No. 10/885,431, mailed Sep. 19, 2007.
Office Action issued in U.S. Appl. No. 10/885,431, mailed Sep. 26, 2008.
Office Action issued in U.S. Appl. No. 10/997,612, mailed Apr. 30, 2007.
Office Action issued in U.S. Appl. No. 10/997,612, mailed Mar. 20, 2008.
Office Action issued in U.S. Appl. No. 10/997,612, mailed May 5, 2006.
Office Action issued in U.S. Appl. No. 10/997,612, mailed Nov. 14, 2008.
Office Action issued in U.S. Appl. No. 10/997,612, mailed Nov. 19, 2007.
Office Action issued in U.S. Appl. No. 10/997,612, mailed Oct. 31, 2006.
Office Action issued in U.S. Appl. No. 11/051,283, mailed Feb. 22, 2006.
Office Action issued in U.S. Appl. No. 11/051,283, mailed Jan. 9, 2008.
Office Action issued in U.S. Appl. No. 11/051,283, mailed Jun. 5, 2009.
Office Action issued in U.S. Appl. No. 11/761,066, mailed Oct. 28, 2008.
Office Action issued in U.S. Appl. No. 11/761,066, mailed Sep. 25, 2007.
Orringer et al., "Management of wounds in patients with complex enterocutaneous fistulas," *Surgery, Gynecology & Obstetrics*, 165:79-80, 1987.
PCT Declaration of Non-Establishment of International Search Report issued in International Application No. PCT/US03/17099, mailed Nov. 7, 2003.
PCT International Preliminary Examination Report issued in International Application No. PCT/GB96/02802, mailed Jan. 15, 1998.
PCT International Preliminary Examination Report issued in International Application No. PCT/US99/17877, mailed Oct. 30, 2001.
PCT International Preliminary Examination Report issued in International Application No. PCT/US00/42333, mailed Nov. 19, 2002.
PCT International Preliminary Examination Report issued in International Application No. PCT/US01/44194, mailed Dec. 3, 2003.
PCT International Search Report issued in International Application No. PCT/GB95/01983, mailed Nov. 23, 1995.
PCT International Search Report issued in International Application No. PCT/GB96/02802, mailed Apr. 29, 1997.
PCT International Search Report issued in International Application No. PCT/GB98/02713, mailed Jan. 8, 1999.
PCT International Search Report issued in International Application No. PCT/US1999/17877, mailed Oct. 27, 1999.
PCT International Search Report issued in International Application No. PCT/US2000/42333, mailed Aug. 3, 2001.
PCT International Search Report issued in International Application No. PCT/US2001/15611, mailed Sep. 5, 2001.
PCT International Search Report issued in International Application No. PCT/US2001/44194, mailed Dec. 9, 2002.
PCT International Search Report issued in International Application No. PCT/US2002/41210, mailed Oct. 28, 2003.
PCT International Search Report issued in International Application No. PCT/US2002/41228, mailed Jun. 30, 2003.
PCT International Search Report issued in International Application No. PCT/US2002/41229, mailed Jun. 30, 2003.

PCT International Search Report issued in International Application No. PCT/US2002/41231, mailed May 9, 2003.
PCT International Search Report issued in International Application No. PCT/US2002/41234, mailed Oct. 24, 2003.
PCT International Search Report issued in International Application No. PCT/US2002/41300, mailed Jul. 31, 2003.
PCT Written Opinion issued in International Application No. PCT/GB96/02802, mailed Sep. 3, 1997.
PCT Written Opinion issued in International Application No. PCT/GB98/02713, mailed Jun. 8, 1999.
PCT Written Opinion issued in International Application No. PCT/US99/17877, mailed Aug. 20, 2001.
PCT Written Opinion issued in International Application No. PCT/US00/42333, mailed Jun. 24, 2002.
Roget's New Millenium Thesaurus, First Edition (v 1.3.1), 2007.
Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).
Schein et al., "The 'Sandwich Technique' in the management of the open abdomen," *British Journal of Surgery*, 73:369-370, 1986.
Search Report issued in Hungarian Application No. P0103545, mailed Oct. 29, 2001.
Search Report issued in Hungarian Application No. P0500055, mailed May 3, 2005.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplementary Search Report issued in European Application No. 02794388.5, mailed Jun. 16, 2009.
Supplementary Search Report issued in European Application No. 02794392.7, mailed Jun. 5, 2009.
Supplementary Search Report issued in European Application No. 02794393.5, mailed Aug. 1, 2006.
Supplementary Search Report issued in European Application No. 02794394.3, mailed Apr. 6, 2009.
Supplementary Search Report issued in European Application No. 02794397.6, mailed Jan. 29, 2009.
Supplementary Search Report issued in European Application No. 02796039.2, mailed Sep. 4, 2009.
Supplementary Search Report issued in European Application No. 07001838.7, mailed Mar. 5, 2007.
Supplementary Search Report issued in European Application No. 08010957.2, mailed Aug. 27, 2008.
Svedman, "A dressing allowing continuous treatment of a biosurface," *IRCS Medical Science: Biomedical Technology, Clinical Medicine, Surgery and Transplantation*, 7:221, 1979.
Svedman, "Irrigation treatment of leg ulcers," *The Lancet*, 2(8349):532-534, 1983.
Tennant, "The use of hypermia in the postoperative treatment of lesions of the extremities and thorax, "*Journal of the American Medical Association*, 64:1548-1549, 1915.
Tribble, "An improved sump drain-irrigation device of simple construction," *Archives of Surgery*, 105(3):511-513, 1972.
Wooding-Scott et al., "No wound is too big for resourceful nurses," *RN*, pp. 22-25, 1988.
Yusupov et al., "Active wound drainage," *Vestnik Khirurgi*, 138(4) (and 7 page English translation thereof), 1987.
Živadinović et al., "Vacuum therapy in the treatment of peripheral blood vessels," *Timok Medical Journal*, 11:161-164 (and copy and certified translation), 1986.
Advisory Action issued in U.S. Appl. No. 10/509,137, mailed Jun. 24, 2010.
Advisory Action issued in U.S. Appl. No. 11/051,283, mailed May 5, 2010.
Communication of Notice of Opposition issued in European Application No. 07001838.7, mailed Apr. 28, 2010 (and copy of Opposition).
Definition of "pore," provided by Merriam-Webster Online Dictionary, printed Apr. 5, 2010.
Definition of "porous," provided by Merriam-Webster Online Dictionary, printed Apr. 5, 2010.
Notice of Allowance issued in U.S. Appl. No. 10/276,778, mailed May 21, 2010.
Notice of Allowance issued in U.S. Appl. No. 10/664,535, mailed Jun. 2, 2010.
Notice of Allowance issued in U.S. Appl. No. 10/885,431, mailed Mar. 22, 2010.
Notice of Allowance issued in U.S. Appl. No. 11/761,066, mailed May 13, 2010.
Office Action issued in Canadian Application No. 2,481,016, mailed Jun. 15, 2010.
Office Action issued in Japanese Application No. 2004-508861, mailed Feb. 16, 2010 (and English language translation thereof).
Office Action issued in U.S. Appl. No. 10/509,137, mailed Apr. 9, 2010.
Office Action issued in U.S. Appl. No. 11/515,983, mailed May 7, 2010.
Office Action issued in U.S. Appl. No. 10/524,957, mailed Jul. 26, 2010.
Office Action issued in U.S. Appl. No. 11/684,989, mailed Jun. 29, 2010.
Supplemental Notice of Allowability issued in U.S. Appl. No. 10/885,431, mailed Apr. 22, 2010.
Office Action issued in Japanese Application No. 2001-539532, mailed May 11, 2010 (and English language translation thereof).
Notice of Allowance issued in U.S. Appl. No. 10/276,778, mailed Sep. 7, 2010.
Notice of Allowance issued in U.S. Appl. No. 10/524,957, mailed Oct. 14, 2010.
Notice of Allowance issued in U.S. Appl. No. 10/664,535, mailed Sep. 9, 2010.
Notice of Allowance issued in U.S. Appl. No. 11/242,543, mailed Sep. 27, 2010.
Notice of Allowance issued in U.S. Appl. No. 11/684,989, mailed Nov. 8, 2010.
Office Action issued in European Application No. 02 794 397.6, mailed Oct. 12, 2010.
Office Action issued in Japanese Application No. 2008-007788, mailed Oct. 5, 2010, and English language translation thereof.
Office Action issued in U.S. Appl. No. 11/051,283, mailed Oct. 15, 2010.
Office Action issued in U.S. Appl. No. 11/515,983, mailed Oct. 5, 2010.
Response to Opposition submitted in European Patent No. EP 1 772 160, filed Sep. 29, 2010.
Office Action issued in U.S. Appl. No. 11/051,283, mailed Mar. 22, 2007.
Office Action issued in U.S. Appl. No. 11/051,283, mailed Oct. 17, 2008.
Office Action issued in U.S. Appl. No. 11/051,283, mailed Sep. 7, 2005.
Office Action issued in U.S. Appl. No. 11/051,283, mailed Sep. 7, 2007.
Office Action issued in U.S. Appl. No. 11/051,283, mailed Sep. 29, 2006.
Office Action issued in U.S. Appl. No. 11/242,543, mailed May 18, 2007.
Office Action issued in U.S. Appl. No. 11/242,543, mailed Oct. 20, 2006.
Office Action issued in U.S. Appl. No. 11/242,543, mailed Oct. 25, 2007.
Office Action issued in U.S. Appl. No. 11/347,073, mailed Apr. 1, 2008.
Office Action issued in U.S. Appl. No. 11/515,983, mailed May 11, 2009.

Office Action issued in U.S. Appl. No. 11/684,989, mailed Jul. 7, 2009.
Office Action issued in U.S. Appl. No. 11/684,989, mailed Nov. 18, 2008.
Office Action issued in U.S. Appl. No. 11/761,066, mailed Dec. 13, 2007.
Office Action issued in U.S. Appl. No. 11/761,066, mailed Jun. 2, 2009.
US 6,216,701, 04/2001, Heaton et al. (withdrawn)

* cited by examiner

WASTE CONTAINER FOR NEGATIVE PRESSURE THERAPY

CROSS REFERENCE TO RELATED APPLICATIONS

This application is a continuation of U.S. patent application Ser. No. 10/267,358, filed Oct. 9, 2002, now abandoned, which claims the benefit of U.S. Provisional Application Ser. No. 60/328,542, filed Oct. 11, 2001, both of which are hereby expressly incorporated by reference herein.

FIELD OF THE INVENTION

The present invention relates to a wound treatment system and specifically to a vacuum therapy wound treatment system for surface wounds. More specifically, the present invention relates to the drainage and collection of exudate from the wound surface through vacuum therapy.

BACKGROUND OF THE DISCLOSURE

Medical professionals, such as nurses and doctors, routinely treat patients having surface wounds of varying size, shape, and severity. It is known that controlling the topical atmosphere adjacent a wound can enhance the healing process. For example, by applying medicinal agents or even water over a wound, dirt and bacteria are either killed or washed away, thereby promoting healing. In addition, applying a negative pressure or vacuum to a wound draws out exudate, which might contain dirt and bacteria, from the wound to further promote healing.

A vacuum bandage is a bandage having a cover for sealing about the outer perimeter of the wound and under which a vacuum is established to act on the wound surface. This vacuum applied to the wound surface accelerates healing of chronic wounds. Typically, suction tubes are provided for drawing exudate away from the wound. If the cover is a flexible cover, which is typically more comfortable for the patient, a porous packing may be provided under the cover to provide the space in which the vacuum is formed. The following U.S. Patents establish the nature of vacuum treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947. All of such references are incorporated herein by reference for purposes of disclosing the nature of such vacuum treatment of wounds.

Figure 1:
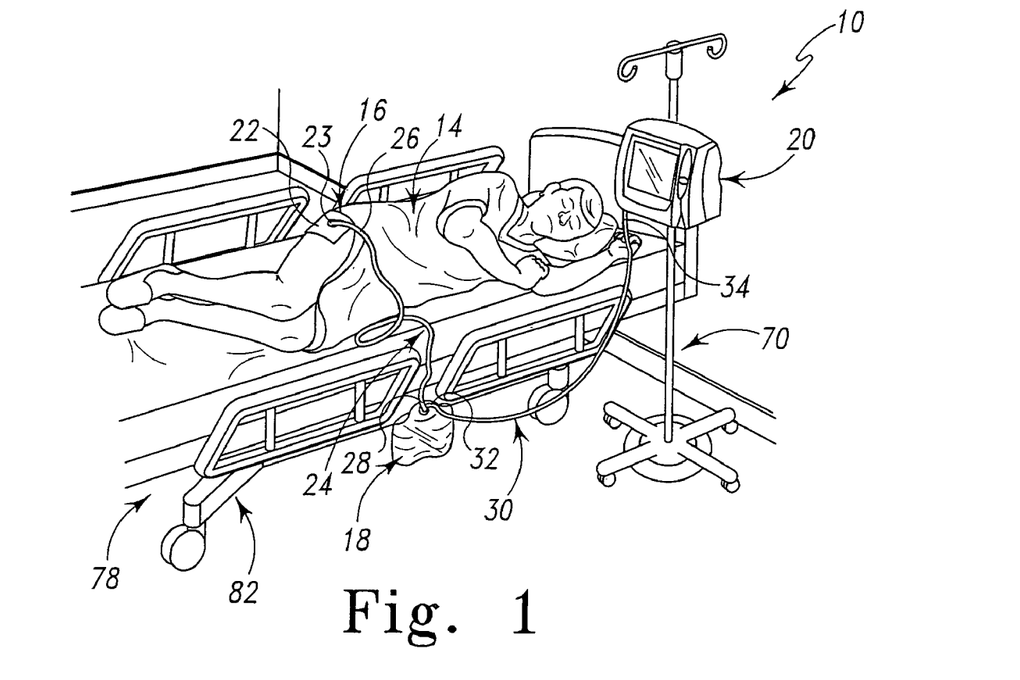
FIG. 1 is a perspective view showing the housing mounted on a mobile IV pole.
Figure 2:
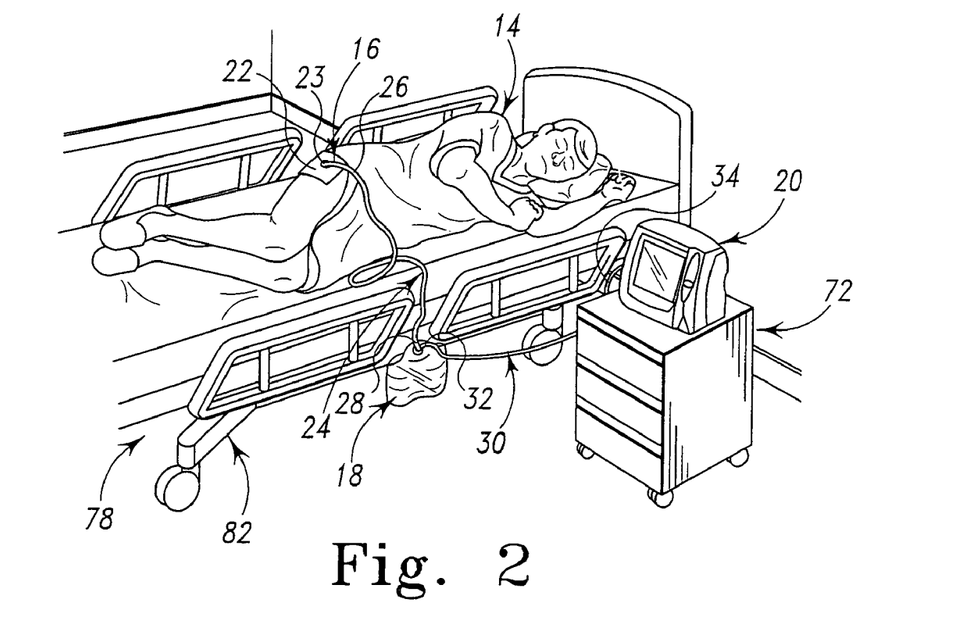
FIG. 2 is a perspective view similar to FIG. 1 showing the housing positioned on a bedside cabinet.
Figure 3:
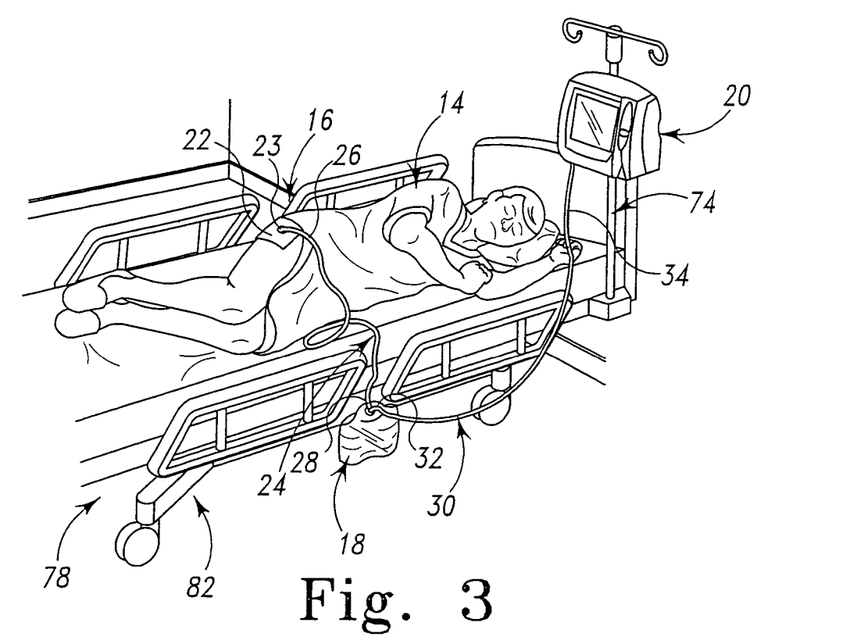
FIG. 3 is a perspective view similar to FIGS. 1 and 2 showing the housing mounted to an on-bed IV pole.
Figure 4:
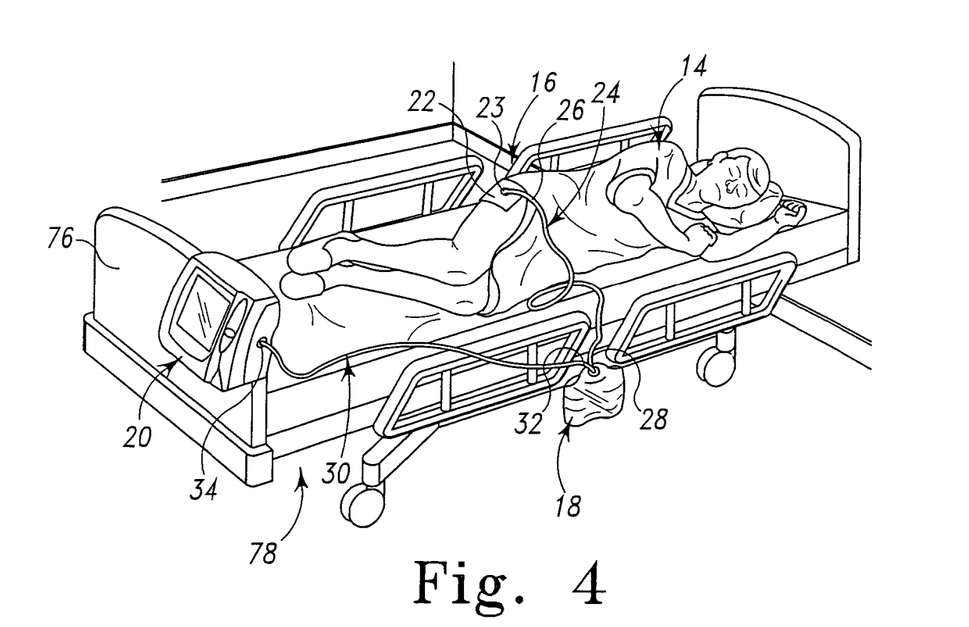
FIG. 4 is a perspective view similar to FIGS. 1-3 showing the housing mounted on a footboard of the patient's hospital bed.

As shown, for example, in U.S. Pat. No. 5,645,081 (hereinafter the '081 patent), a method of treating tissue damage is provided by applying negative pressure to a wound. The negative pressure is provided in sufficient duration and magnitude to promote tissue migration in order to facilitate the closure of the wound. FIG. 1 of the '081 patent discloses an open cell polyester foam section covering the wound, a flexible hollow tube inserted into the foam section at one end and attached to a vacuum pump at another end, an adhesive sheet overlying the foam section, and tubing to adhere to the skin surrounding the wound in order to form a seal that allows the creation of a vacuum when the suction pump is operating. The '081 patent further teaches use of negative pressure between about 0.1 and 0.99 atmospheres, and that the pressure can be substantially continuous, wherein the pressure is relieved only to change the dressing on the wound. Alternatively, the '081 patent teaches use of a cyclic application of pressure in alternating periods of application and non-application. In a preferred embodiment, pressure is applied in 5 minute periods of application and non-application.

Various other prior art references teach the value of the vacuum bandage or the provision of vacuum to the surface of a chronic wound. Several Russian language articles exist that establish the efficacy of vacuum therapy. Examples of such prior art articles, each of which discusses the use of application of vacuum to a wound to promote healing, are as follows: "Vacuum therapy in the treatment of acute suppurative diseases of soft tissues and suppurative wound", Davydov, et al. Vestn. Khir., September 1988 (the September 1988 article); "Pathenogenic mechanism of the effect of vacuum therapy on the course of the wound process", Davydov, et al. Khirurigiia, June 1990 (the June 1990 article); and "Vacuum therapy in the treatment of suppurative lactation mastitis", Davydov, et al., Vestn. Khir., November 1986 (the November 1986 article).

The Russian articles distinguish wound drainage from the use of vacuum therapy for healing. The Russian authors report that vacuum therapy resulted in faster cleansing of the wound and more rapid detoxification than with the traditional incision-drainage method. The November 1986 article describes the vacuum therapy techniques as a reduction of 0.8-1.0 atmosphere for 20 minutes at the time of surgery, and subsequent 1.5 to 3 hour treatments at a reduced pressure of 0.1 to 0.15 from atmosphere, twice daily. These Russian articles teach the use of negative pressure to effect healing. The articles describe using several sessions per day, each lasting up to one hour, with a vacuum of 76-114 mmHg.

The Russian articles teach using this vacuum method to decrease the number of microbes in the wound. The June 1990 article teaches that vacuum therapy provides a significant antibacterial effect. The June 1990 article describes the stepped up inflow of blood to the zone around the wound, which leads to an increase in the number of leukocytes reaching the focus of inflammation. Subsequent articles and patents further develop the benefits obtained with vacuum therapy. The prior art, therefore, teaches the benefit and value of a vacuum bandage.

SUMMARY OF THE DISCLOSURE

Accordingly, a vacuum therapy system for treating a patient with a wound is provided. The system includes a vacuum bandage comprising a cover to seal about the wound. The cover also defines a space above the wound in which a vacuum is to be formed. The bandage further comprises a port which provides communication with the space. The system further includes a receptacle to be placed below the wound. The receptacle is connected to the port to receive exudate from the wound. Finally, the system includes a vacuum source spaced apart from the receptacle and connected to the receptacle. The vacuum source is effective to provide a vacuum in the receptacle and in the space above the wound.

Illustratively, the system may comprise one or more of the following features alone or in combination with each other: a first tube coupled to the port of the bandage and the receptacle, a second tube coupled to the vacuum source and the receptacle, a means for attaching the receptacle to a support below the wound, a means for supporting the vacuum source away from the receptacle, and/or a control dominating the vacuum source to establish the amount of vacuum applied to the space and the time when the vacuum is applied to the space.

Further illustratively, the receptacle of the system may comprise one or more of the following features alone or in combination with each other: an anti-microbial filter, an air vent to allow an inner area of the receptacle to communicate with the surrounding atmosphere, a mounting portion, and an upper portion and a lower portion coupled to the upper portion. The anti-microbial filter may be hydrophobic, and the upper portion of the receptacle may be made of a rigid material while the lower portion of the receptacle may be made of a flexible material.

The vacuum source of the system may comprise a vacuum pump and associated controls and/or a flow sensor to be connected to a vacuum line. Illustratively, the flow sensor may be configured to determine the level of vacuum present in the receptacle.

A method for treating a wound on a patient is also provided including the steps of sealing a bandage having a port about the wound to define a space above the wound in which a vacuum can be formed, placing a receptacle below the wound, and placing a vacuum source spaced away from the receptacle. The method further includes the steps of connecting the receptacle to the port of the bandage, connecting the vacuum source to the receptacle, and operating the vacuum source to evacuate the receptacle and provide a vacuum in the space above the wound. The method further includes the step of controlling the level of vacuum applied to the space and the time of application of the vacuum.

Additional features and advantages of the apparatus will become apparent to those skilled in the art upon consideration of the following detailed descriptions exemplifying the best mode of carrying out the apparatus as presently perceived.

BRIEF DESCRIPTION OF THE DRAWINGS

The detailed description particularly refers to the accompanying figures in which:

FIGS. 1-4 are perspective views of a vacuum therapy system and a patient undergoing vacuum therapy treatment showing a vacuum bandage of the system coupled to the patient, a waste drainage container or receptacle coupled to the vacuum bandage by a first tube and a housing including a vacuum source coupled to the receptacle by a second tube, and also showing the receptacle positioned below the wound and spaced apart from housing;

DETAILED DESCRIPTION OF THE DRAWINGS

A vacuum therapy system 10 is provided for use with a wound on a patient 14, as shown in FIGS. 1-4. System 10 comprises a vacuum bandage 16, a waste container or receptacle 18 coupled to the bandage 16, and a housing 20 coupled to the receptacle 18. Housing 20 includes a vacuum source 21 (shown in FIG. 5) for applying negative pressure to the wound to draw exudate from the wound in order to facilitate healing. Receptacle 18 is provided to collect the exudate drawn from the wound and is placed below the wound to facilitate the drainage of exudate from the wound by gravity as well as suction. Housing 20, which includes the vacuum source 21, is spaced apart from receptacle 18 in order to allow a caregiver to place the housing 20 in any convenient location while still benefiting from the gravitational effects gained by maintaining the receptacle 18 at a level below the wound.

Illustrative vacuum bandages and vacuum and irrigation systems are disclosed in U.S. patent application Ser. No. 09/725,352 to Lockwood, et al. titled "VACUUM THERAPY AND CLEANSING DRESSING FOR WOUNDS", U.S. patent application Ser. No. 09/725,666 to Risk et al. titled "WOUND TREATMENT APPARATUS", and U.S. patent application Ser. No. 09/369,113 to Henley et al. titled "WOUND TREATMENT APPARATUS". Each of these applications are assigned to the same assignee as the present application and are specifically incorporated herein by reference.

Vacuum bandage 16 includes a cover 22 to seal about the wound. The bandage 16 operates to define a space above the wound to which negative pressure can be applied to form a vacuum. The bandage 16 further includes a port 23 in communication with the space above the wound. The port 23 is coupled to receptacle 18 by a first tube 24 of the system 10. First tube 24 includes a first end 26 coupled to the port 23 and a second end 28 coupled to the receptacle 18. System 10 further includes a second tube 30 coupled at a first end 32 to the receptacle 18 and coupled at a second end 34 to the vacuum source 21 which may be contained within housing 20.

Illustrative receptacle 18 of the vacuum therapy system 10 includes a body 40 which forms an interior cavity 42 for collecting exudate 62 (shown in FIG. 5) and fluid drawn from the wound therein. Although receptacle 18 is illustratively shown in FIG. 5, the height, width, and shape of receptacle 18 may take various forms. Body 40 includes an upper portion 44 and a lower portion 46 coupled to the upper portion 44. Upper portion 44 defines an inlet port 48 coupled to the first tube 24, and an outlet port 50 coupled to the second tube 26. In illustrative embodiments, upper portion 44 of the receptacle 18 is formed from a rigid material and the lower portion 46 of the receptacle 18 is also formed from a rigid material and is integral with the upper portion 44, as shown, for example, in FIGS. 5-7. However, it is within the scope of this disclosure to include a receptacle having a lower portion 46 made from a flexible material as well. For example, lower portion 46 may be a flexible bag removably coupled to the upper portion 44 of receptacle 18.

Figure 5:
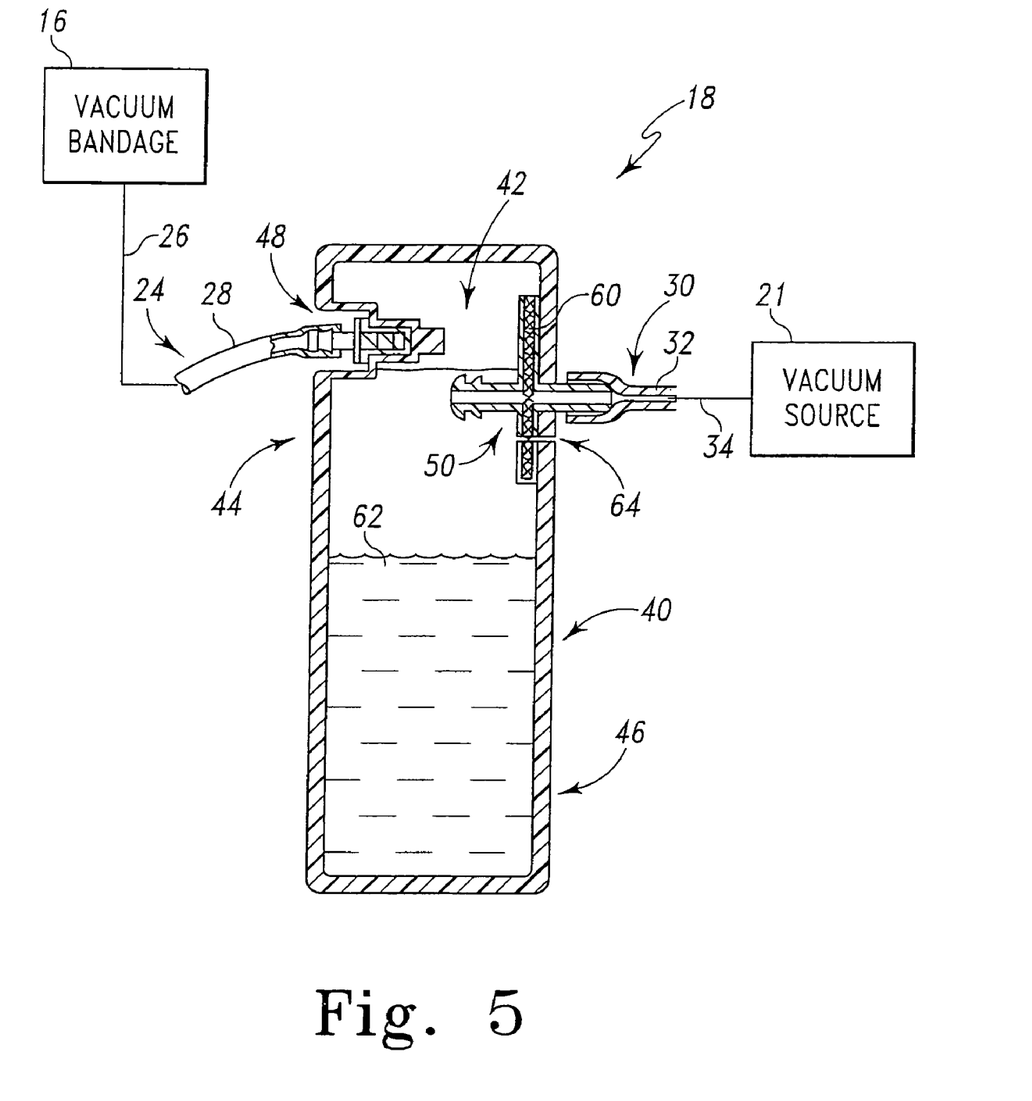
FIG. 5 is a sectional view of an illustrative receptacle showing the first tube coupled to an inlet port of the receptacle and showing the second tube coupled to an outlet port of the receptacle and also showing a hydrophobic filter positioned at the outlet port of the receptacle.

As shown in FIG. 5, receptacle 18 further includes a hydrophobic filter 60 in communication with second tube 30 and thus the vacuum source 21. Illustratively, filter 60 is a 0.2-micron hydrophobic anti-microbial filter. Upper portion 44 of receptacle 18 further defines an air vent 64 to provide communication between interior cavity 42 of receptacle 18 and the outside atmosphere. Preferably, as shown in FIG. 5, hydrophobic filter 60 is positioned over air vent 64 to prevent bacteria, etc. in the surrounding atmosphere from entering receptacle 18.

As mentioned above, first end 32 of second tube 30 is coupled to outlet port 50 of receptacle 18 and second end 34 of second tube 30 is coupled to vacuum source 21. Vacuum source 21 may be contained within housing 20 or may be external to the housing 20. For example, most medical facilities have vacuum ports near where patients are treated, such as in-wall vacuum ports, for example. Each port is served by a system vacuum pump to provide negative pressure. Vacuum source 21 is also defined to include any type of mechanism for providing negative pressure such as an electrically operated or manual pump, for example. Housing 20 is configured to be a portable unit allowing a caregiver to move housing 20 to wherever the patient is located within close proximity to the wound or wounds. For example, as shown in FIGS. 1-4, the housing 20 is shown to be coupled to a mobile IV pole 70, positioned on a bedside cabinet 72, coupled to an on-bed IV pole 74, and coupled to a footboard 76 of the hospital bed 78. Each of the mobile IV pole 70, cabinet 72, in-bed IV pole 74, and footboard 76 illustrate an example of a means for supporting the housing 20 and vacuum source 21 away from receptacle 18. The housing 20 and its vacuum source 21 may be placed above, at generally the same level, or below the receptacle 18. Preferably, the receptacle 18 will be placed below the wound.

In addition to the vacuum source 21, it is also within the scope of the disclosure for housing 20 to include a controller (not shown) for controlling the amount and rate of negative pressure to be applied to the wound, for example. Housing 20 may also include an irrigation system and such other devices and components as disclosed in U.S. patent application Ser. No. 09/725,666, referenced above and incorporated herein.

As described above, the components of system 10 (vacuum bandage 16, first tube 24, receptacle 18, second tube 30, and vacuum source 21) are coupled to each other in series. The port of vacuum bandage 16 is coupled to the receptacle 18 by first tube 24. First tube 24 is coupled to inlet port 48 of receptacle 18 and receptacle 18 is coupled to the housing 20, or more specifically, to the vacuum source 21, by second tube 30. First end 32 of second tube 30 is coupled to outlet port 50 of receptacle 18 and second end 34 of second tube 30 is coupled to vacuum source 21. By this series configuration, the vacuum source 21 is thus in fluid communication with the receptacle 18 through the second tube 3, and the space above the wound created by vacuum bandage 16 is in fluid communication with receptacle 18 through first tube 24. Therefore, the vacuum source 21 operates to create negative pressure, or a vacuum, in the space above the wound, in the first tube 24, in receptacle 18, and in second tube 30.

Illustratively, a flow sensor (not shown) may be coupled to second tube 30 between receptacle 18 and vacuum source 21 for monitoring the fluid flow from receptacle 18 to vacuum source 21. The flow sensor may then provide feedback to the controller, for example, located within housing 20. If, for example, the flow sensor detects no fluid flow, the feedback sent to the controller would signal the vacuum source 21 to turn off or cease running.

In operation, it is possible that at a period of time after negative pressure is created above the wound, system 10 may become relatively static due to a lack of fluid flow through system 10. As mentioned above, this lack of fluid flow could cause the vacuum source 21 to be turned off. However, it may still be beneficial to provide a vacuum above the wound in order to draw blood up to the surface of the wound. Air vent 64 is provided in receptacle 18 in order to maintain a small amount of fluid flow to prevent the flow sensor from detecting a static system. Once system 10 has become relatively static and there is little to no fluid flow from bandage 16 through first tube 24 and to receptacle 18, vacuum source 21 is still able to pull air through air vent 64 thus allowing the flow sensor to detect a fluid flow in order to keep the vacuum source 21 running. Once the level of exudate 62 collected within receptacle 18 reaches air vent 64 and/or outlet port 50, hydrophobic filter 60 will prevent liquid to pass therethrough and the flow sensor will sense that the flow has become static. The flow sensor will send a signal to the controller which will, in turn, tell the vacuum source 21 to turn off.

In use, receptacle 18 is positioned below the vacuum bandage 16 and the patient's wound to which the vacuum bandage 16 is attached. As shown in FIGS. 1-4, placing receptacle 18 below the wound facilitates the drainage of exudate from the wound through gravity. Therefore, exudate is drawn from the wound through the use of a negative pressure supplied by vacuum source 21 and through the use of gravity. Receptacle 18 is also spaced apart from vacuum source 21 and/or the housing 20, as shown in FIGS. 1-4. As stated above, vacuum source 21 is often provided within housing 20. Therefore, spacing receptacle 18 apart from the vacuum source 21 allows the housing 20 to be placed at any desired location or level while still maintaining use of gravity for the collection of exudate within receptacle 18.

Figure 6:
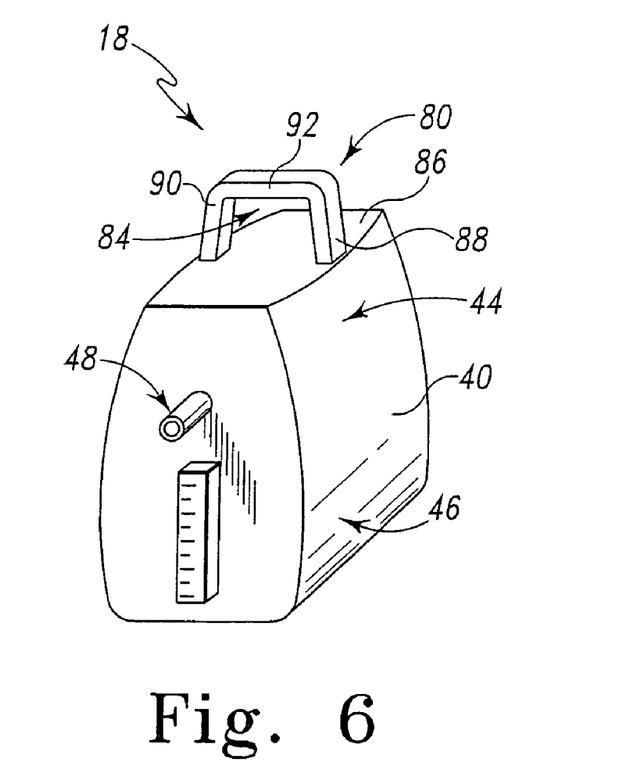
FIG. 6 is a perspective view of another illustrative waste receptacle of the present invention showing a mounting portion of the receptacle for mounting the receptacle to a bed frame of the hospital bed, as shown in FIGS. 1-4.
Figure 7:
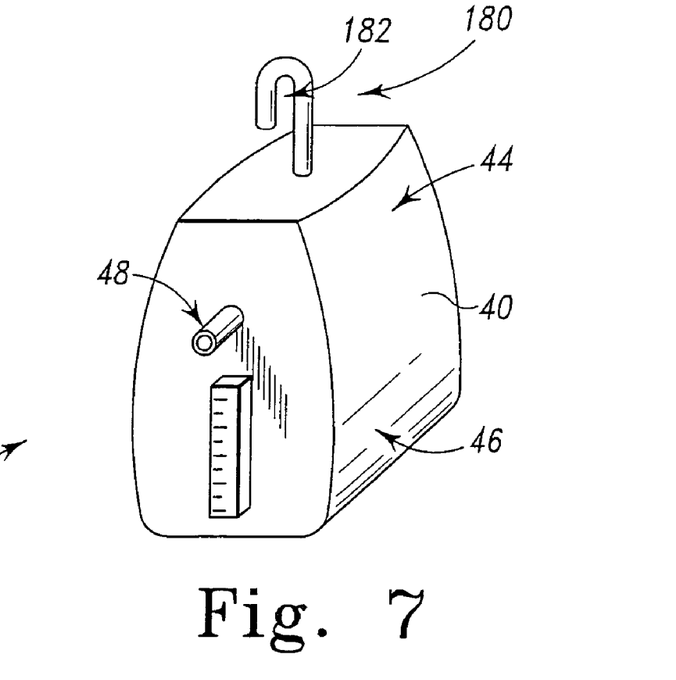
FIG. 7 is a perspective view of yet another illustrative waste receptacle of the present invention showing an alternative mounting portion of the receptacle for mounting the receptacle to the bed frame of the hospital bed.

In illustrative embodiments, receptacle 18 includes a mounting portion 80 coupled to the body 40, as shown in FIGS. 6 and 7. Mounting portion 80 is provided to allow a caregiver to mount the receptacle 18 to hospital bed 78 below the patient 14 and thus below the wound in order to facilitate the drainage of the exudate from the wound by gravity. Hospital beds 78 often to include a hook (not shown) or a type of mount or support coupled to a bed frame 82 of the bed 78. Urine bags, for example, are often hung by the caregiver from these hooks to facilitate drainage through the use of gravity alone.

Mounting portion 80 of receptacle 18, as shown in FIG. 6, is in the shape of a handle to define an aperture 84 for receiving the hook or mount coupled to bed frame 82. Mounting portion 80 is coupled to a top wall 86 of body 40 to cooperate with body 40 and form aperture 84. Mounting portion 80 includes a first generally vertical member 88 coupled to top wall 86, a second generally vertical member 90 coupled to top wall 86, and a generally horizontal member 92 spaced-apart from top wall 86 and coupled to and positioned to extend between each of the first and second generally vertical members 88, 90.

Another illustrative mounting portion 180 is shown in FIG. 7. Alternate mounting portion 180 is hook-shaped and includes a single curved member coupled to the top wall 86 of the receptacle 18 to define a hook-receiving space 182 for receiving a hook or mount of the bed frame 82. Although mounting portion 80 and alternate mounting portion 180 are disclosed and described herein, it is within the scope of this disclosure to include a receptacle having a mounting portion adapted to cooperate with the bed frame of the hospital bed in order to support the receptacle below the wound of the patient being treated.

Although the invention has been described in detail with reference to certain preferred embodiments, variations and modifications exist within the scope and spirit of the invention.

The invention claimed is:

1. A system for treating a patient with a wound, the system comprising:
    (a) a bandage comprising a cover to seal about the wound and define a space above the wound in which a vacuum is to be formed, and a port providing communication with the space,
    (b) a receptacle positioned at an elevation below the wound, the receptacle comprising a body having an upper portion and a lower portion including a wound exudate-collecting cavity, the upper portion having an inlet port, an outlet port and an air vent in direct communication with the wound exudate-collecting cavity and configured for communication with the surrounding atmosphere, the inlet port being connected to the port of the bandage to receive exudate from the wound, (c) a vacuum source connected to the outlet port of the receptacle, the vacuum source positioned at an elevation vertically higher than the receptacle and being effective to provide a vacuum in the receptacle and in the space and to pull air from the surrounding atmosphere into the wound exudate-collecting cavity of the receptacle through the air vent as wound exudate is received through the inlet port into the wound exudate-collecting cavity of the receptacle, and (d) a housing spaced apart from the receptacle and carrying the vacuum source, the housing not carrying the receptacle.

2. The system of claim 1, further including a first tube coupled to the port of the bandage and the inlet port of the receptacle and a second tube coupled to the vacuum source and the outlet port of the receptacle.

3. The system of claim 1, wherein the receptacle further includes a mounting portion for attaching the receptacle to a support.

4. The system of claim 1, wherein the receptacle further includes an anti-microbial filter adjacent the outlet port.

5. The system of claim 4, wherein the filter is hydrophobic.

6. A system for treating a patient with a wound, the system comprising:
(a) a bandage comprising a cover to seal about the wound and define a space above the wound in which a vacuum is to be formed, and a port providing communication with the space,
(b) a receptacle positioned at an elevation below the wound, the receptacle comprising a body having an upper portion and a lower portion, the upper portion having an inlet port, an outlet port and an air vent, the inlet port being connected to the port of the bandage to receive exudate from the wound,
(c) a vacuum source connected to the outlet port of the receptacle, the vacuum source positioned at an elevation vertically higher than the receptacle and being effective to provide a vacuum in the receptacle and in the space and to pull air into the receptacle through the air vent as wound exudate is received through the inlet port into the receptacle, and
(d) a housing spaced apart from the receptacle and carrying the vacuum source, the housing not carrying the receptacle,
wherein the receptacle further includes an anti-microbial filter adjacent the outlet port, and
wherein the air vent is positioned adjacent the outlet port and the anti-microbial filter is positioned over the air vent.

7. The system of claim 1, wherein the upper portion of the receptacle is formed from a rigid material.

8. The system of claim 7, further comprising a support for supporting the housing carrying the vacuum source away from the receptacle and at an elevation vertically higher than the receptacle.

9. The system of claim 7, wherein the lower portion of the receptacle is formed from a flexible material.

10. The system of claim 1, wherein the vacuum bandage, receptacle, and vacuum source are configured to operate in series with each other.

11. The system of claim 1, comprising a control dominating the vacuum source, the control being configured to establish the amount of vacuum applied to the space.

12. The system of claim 11, wherein the control is configured to establish the time when vacuum is applied to the space.

13. A method for treating a wound on a patient, the method comprising the steps of:
(a) sealing a bandage having a port about the wound to define a space above the wound and in communication with the port in which a vacuum can be formed,
(b) placing a receptacle below and away from the wound, the receptacle having an inlet port, an outlet port and an air vent,
(c) placing a portable housing carrying a vacuum source, the vacuum source positioned at an elevation vertically higher than the receptacle, the housing not carrying the receptacle,
(d) connecting the inlet port of the receptacle to the port of the bandage,
(e) connecting the vacuum source to the outlet port of the receptacle, and
(f) operating the vacuum source to provide a vacuum in the receptacle and in the space above the wound and to pull air into the receptacle through the air vent.

14. The method of claim 13, comprising the step of controlling the level of vacuum applied to the space and the time of application of the vacuum.

15. The system of claim 1, wherein the vacuum source is positioned at an elevation vertically higher than the bandage.

16. A system for creating a vacuum above a wound and drawing exudate away from the wound, the system comprising:
(a) a vacuum bandage to place over and seal about the wound on a patient to provide a vacuum space above the wound and a port communicating with the space,
(b) a receptacle positioned at an elevation below the wound, the receptacle having an inlet port and an outlet port, the inlet port of the receptacle being in communication through the port of the bandage with the vacuum space,
(c) a vacuum source connected to the outlet port of the receptacle, the vacuum source positioned at an elevation vertically higher than the receptacle and operable to provide a vacuum in the receptacle and in the vacuum space, thereby subjecting a surface of the wound to vacuum therapy, and
(d) a portable housing spaced apart from the receptacle and carrying the vacuum source, the housing not carrying the receptacle;
wherein the vacuum source comprises a vacuum pump and associated controls, the pump being connected to the outlet port of the receptacle
wherein the vacuum source is positioned at an elevation vertically higher than the bandage.

* * * * *